(12) United States Patent
Burckhardt

(10) Patent No.: US 8,157,950 B2
(45) Date of Patent: Apr. 17, 2012

(54) ALDIMINE AND COMPOSITION CONTAINING ALDIMINE

(75) Inventor: Urs Burckhardt, Zürich (CH)

(73) Assignee: Sika Technology AG, Baar (CH)

( * ) Notice: Subject to any disclaimer, the term of this patent is extended or adjusted under 35 U.S.C. 154(b) by 0 days.

(21) Appl. No.: 13/151,919

(22) Filed: Jun. 2, 2011

(65) Prior Publication Data

US 2011/0253309 A1 Oct. 20, 2011

Related U.S. Application Data

(63) Continuation of application No. PCT/EP2009/066185, filed on Dec. 2, 2009.

(30) Foreign Application Priority Data

Dec. 2, 2008 (EP) .................................... 08170476

(51) Int. Cl.
| | |
|---|---|
| C09J 4/00 | (2006.01) |
| C09J 101/00 | (2006.01) |
| C09J 201/00 | (2006.01) |
| C07D 345/00 | (2006.01) |
| C07D 517/00 | (2006.01) |
| C07D 293/00 | (2006.01) |
| C07D 421/00 | (2006.01) |

(52) U.S. Cl. ......... 156/330.9; 525/452; 540/1; 548/100; 564/248

(58) Field of Classification Search ................ 156/330.9; 525/452; 564/248, 471; 540/1; 548/100
See application file for complete search history.

(56) References Cited

U.S. PATENT DOCUMENTS

| | | | |
|---|---|---|---|
| 4,224,417 | A | 9/1980 | Hajek et al. |
| 6,136,942 | A | 10/2000 | Pfenninger et al. |
| 2006/0149025 | A1 | 7/2006 | Burckhardt |
| 2009/0176944 | A1 | 7/2009 | Burckhardt |

FOREIGN PATENT DOCUMENTS

| | | | |
|---|---|---|---|
| DE | 1670133 | A1 | 7/1970 |
| DE | 2546536 | A1 | 4/1977 |
| EP | 0947529 | A1 | 10/1999 |
| EP | 1975190 | A1 | 10/2008 |
| WO | WO 2004/013088 | A1 | 2/2004 |
| WO | WO 2007/036571 | A1 | 4/2007 |

OTHER PUBLICATIONS

Möhrle et al., "Die Aminomethylierung von Isobutyraldehyd mit freien primären Aminen in homogenem und heterogenem Medium. Über Mannichbasen XI" Die Pharmazie (Nov. 1975), vol. 30, No. 11, pp. 699-706.
Notification of Transmittal of Translation of the International Preliminary Report on Patentability (Forms PCT/IB/338 and PCT/IB/373) and the Written Opinion of the International Searching Authority ( Form PCT/ISA/237) issued on Jun. 16, 2011, in the corresponding International Application No. PCT/EP2009/066185.
International Search Report (PCT/ISA/210) issued on Mar. 1, 2010, by European Patent Office as the International Searching Authority for International Application No. PCT/EP2009/066185.
Written Opinion (PCT/ISA/237) issued on Mar. 1, 2010, by European Patent Office as the International Searching Authority for International Application No. PCT/EP2009/066185.

*Primary Examiner* — Philip Tucker
*Assistant Examiner* — Michael Orlando
(74) *Attorney, Agent, or Firm* — Buchanan Ingersoll & Rooney PC

(57) ABSTRACT

Aldimines of Formula (I), which can be used as latent curing agents in curing compositions, for example, in moisture-curing polyurethane compositions that have isocyanate groups. The aldimines are compounds that can be liquid at room temperature, can have a hardly noticeable aldehyde odor before, during and after hydrolysis, and can have a long shelf life. An aldehyde in polyurethane compositions that is released during hydrolysis has only a slight softening effect and can exhibit very little tendency to migrate or exude.

24 Claims, No Drawings

ALDIMINE AND COMPOSITION CONTAINING ALDIMINE

RELATED APPLICATIONS

This application claims priority as a continuation application under 35 U.S.C. §120 to PCT/EP2009/066185, which was filed as an International Application on Dec. 2, 2009 designating the U.S., and which claims priority to European Application No. 08170476.9 filed in Europe on Dec. 2, 2008. The entire contents of these applications are hereby incorporated by reference in their entireties.

FIELD

This disclosure relates to the field of aldimines and the field of polyurethane compositions as well as the use thereof, for example, as adhesive, sealant, coating, or floor covering.

BACKGROUND INFORMATION

Aldimines are condensation products that include primary amines and aldehydes and represent a family of substances that has been known. Upon contact with moisture, aldimines can hydrolyze to form the corresponding amines and aldehydes. Based on this characteristic, they can be used as a protected form of amines, or of aldehydes. Thus, for example, aldimines are used in polyurethane chemistry, where they are used as cross-linking agents that can be activated by moisture, so-called "blocked amines" or "latent curing agents," for single- or two-component compositions that have isocyanate groups.

Advantages of using aldimines as latent curing agents in systems that have isocyanate groups lie, for example, in that the development of undesirable gas bubbles can be reduced or avoided, since the curing reaction with the blocked amine—in contrast to the direct reaction of isocyanates with moisture—does not run with release of carbon dioxide ($CO_2$), and in that higher curing speeds and/or longer open times can be achieved. The use of aldimines as latent curing agents in compositions that have isocyanate groups can also cause problems, however. In the case of single-component compositions, the shelf life can be greatly limited by the presence of aldimine. Based on the aldehydes used for the production of aldimine and released again during the curing reaction, the compositions can have a very strong odor, moreover, which cannot be tolerated for many applications.

WO 2004/013088 A1 describes odorless polyaldimines, which are produced from primary polyamines and odorless aldehydes.

WO 2007/036571 A1 describes odorless aldimines that contain at least one hydroxyl, mercapto or secondary amino group, which also are available starting from odorless aldehydes. These odorless aldehydes can have a strongly softening effect in polymer compositions, for example, in polyurethane compositions, which may be undesirable. The relatively high molecular weight of the aldehydes results, moreover, in that the aldimines produced therefrom as latent curing agents may have to be used in a relatively large amount, which can make their use expensive.

SUMMARY

According to an exemplary aspect, an aldimine of Formula (I) is disclosed

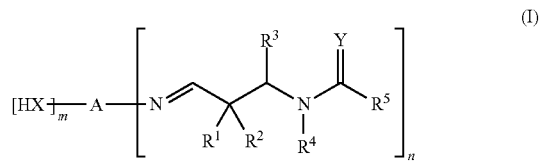

wherein
Y represents O or S;
A either
represents the (n+m)-value radical of an amine after removal of n primary amino groups and m HX groups,
or together with $R^7$ represents an (n+2*m)-value hydrocarbon radical with 3 to 20 C atoms, which optionally contains at least one heteroatom;
$R^1$ and $R^2$ either
independently of one another in each case represents a monovalent hydrocarbon radical with 1 to 12 C atoms,
or together represent a divalent hydrocarbon radical with 4 to 12 C atoms, which is part of an optionally substituted, carbocyclic ring with 5 to 8 C atoms;
$R^3$ stands for a hydrogen atom or an alkyl, cycloalkyl, arylalkyl or alkoxycarbonyl radical with 1 to 12 C atoms;
$R^4$ and $R^5$ either
together represent a divalent radical with 2 to 10 C atoms that optionally has oxygen or sulfur atoms and that is part of an optionally substituted, 5- or 6- or 7-membered ring,
or
$R^4$ represents an alkyl, cycloalkyl, arylalkyl or acyl radical with 1 to 10 C atoms, and
$R^5$ represents a hydrogen atom or for a monovalent radical with 1 to 20 C atoms selected from the group consisting of an alkyl, cycloalkyl, arylalkyl, aryl radical, —$OR^{5'}$, —$SR^{5'}$ and —$NR^{5'}R^{5''}$,
wherein $R^{5'}$ and $R^{5''}$ either in each case represents a hydrocarbon radical or together represent an alkylene radical, which is part of a 5-, 6- or 7-membered ring;
X represents O or S or N—$R^6$ or N—$R^7$,
wherein $R^6$
either
represents a monovalent hydrocarbon radical with 1 to 20 C atoms, which has optionally at least one carboxylic acid ester, nitrile, nitro, phosphonic acid ester, sulfone or sulfonic acid ester group,
or represents a substituent of Formula (II),

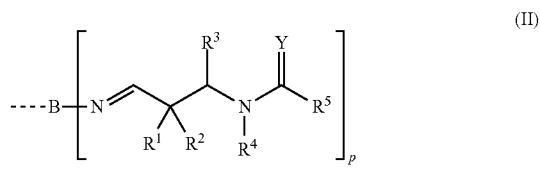

wherein p stands for 0 or for an integer from 1 to 10,000, and

B stands for a (p+1)-value hydrocarbon radical, which optionally contains ether-oxygen, tertiary amine-nitrogen, hydroxyl groups, secondary amino groups or mercapto groups; and $R^7$ together with A stands for an (n+2*m)-value hydrocarbon radical with 3 to 20 C atoms, which optionally contains at least one heteroatom;

n stands for 1 or 2 or 3 or 4, and m stands for 0 or 1 or 2 or 3 or 4, provided that m+n stands for 2 or 3 or 4 or 5.

According to an exemplary embodiment, a single-component, moisture-curing composition is disclosed, comprising a) at least one polyisocyanate P, and b) at least one aldimine of Formula (I b)

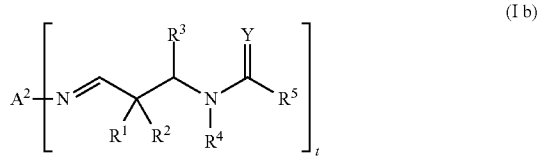

(I b)

wherein t represents 2 or 3;

$A^2$ represents a radical of an amine B2 after removal of t primary amino groups, provided that the aldimine of Formula (I b) does not have any active hydrogen, Y represents O or S;

$R^1$ and $R^2$ either independently of one another in each case represents a monovalent hydrocarbon radical with 1 to 12 C atoms, or together represent a divalent hydrocarbon radical with 4 to 12 C atoms, which is part of an optionally substituted, carbocyclic ring with 5 to 8 C atoms;

$R^3$ stands for a hydrogen atom or an alkyl, cycloalkyl, arylalkyl or alkoxycarbonyl radical with 1 to 12 C atoms;

$R^4$ and $R^5$ either together represent a divalent radical with 2 to 10 C atoms that optionally has oxygen or sulfur atoms and that is part of an optionally substituted, 5- or 6- or 7-membered ring, or $R^4$ represents an alkyl, cycloalkyl, arylalkyl or acyl radical with 1 to 10 C atoms, and $R^5$ represents a hydrogen atom or for a monovalent radical with 1 to 20 C atoms selected from the group consisting of an alkyl, cycloalkyl, arylalkyl, aryl radical, —$OR^{5'}$, —$SR^{5'}$ and —$NR^{5'}R^{5''}$, wherein $R^{5'}$ and $R^{5''}$ either in each case represents a hydrocarbon radical or together represent an alkylene radical, which is part of a 5-, 6- or 7-membered ring;

and/or at least one addition product AV of Formula (XII)

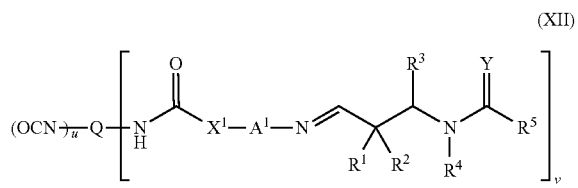

(XII)

wherein Q represents a radical of a (u+v) polyisocyanate P that has isocyanate groups after removal of all isocyanate groups;

u represents 0 or 1 or 2 or 3, v represents 1 or 2 or 3 or 4, provided that (u+v) represents 2 or 3 or 4, $A^1$ either represents a divalent hydrocarbon radical with 2 to 20 C atoms, which optionally contains at least one heteroatom, or together with $R^9$ represents a trivalent hydrocarbon radical with 3 to 20 C atoms, which optionally contains at least one heteroatom, $X^1$ represents O or S or N—$R^8$ or N—$R^9$, wherein $R^8$ either represents a monovalent hydrocarbon radical with 1 to 20 C atoms, which optionally has at least one carboxylic acid ester, nitrile, nitro, phosphonic acid ester, sulfone or sulfonic acid ester group, or represents a substituent of Formula (II a),

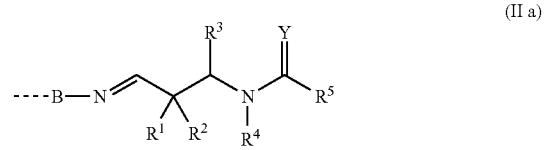

(II a)

wherein $B^1$ stands for a divalent hydrocarbon radical with 2 to 12 C atoms that optionally has ether-oxygen or tertiary amine-nitrogen; and $R^9$ together with $A^1$ represents a trivalent hydrocarbon radical with 3 to 20 C atoms, which optionally contains at least one heteroatom;

provided that $A^1$ does not have any active hydrogen

Y represents O or S;

$R^1$ and $R^2$ either independently of one another in each case represents a monovalent hydrocarbon radical with 1 to 12 C atoms, or together represent a divalent hydrocarbon radical with 4 to 12 C atoms, which is part of an optionally substituted, carbocyclic ring with 5 to 8 C atoms;

$R^3$ stands for a hydrogen atom or an alkyl, cycloalkyl, arylalkyl or alkoxycarbonyl radical with 1 to 12 C atoms;

$R^4$ and $R^5$ either together represent a divalent radical with 2 to 10 C atoms that optionally has oxygen or sulfur atoms and that is part of an optionally substituted, 5- or 6- or 7-membered ring, or $R^4$ represents an alkyl, cycloalkyl, arylalkyl or acyl radical with 1 to 10 C atoms, and $R^5$ represents a hydrogen atom or for a monovalent radical with 1 to 20 C atoms selected from the group consisting of an alkyl, cycloalkyl, arylalkyl, aryl radical, $-OR^{5'}$, $-SR^{5'}$ and $-NR^{5'}R^{5''}$, wherein $R^{5'}$ and $R^{5''}$ either in each case represents a hydrocarbon radical or together represent an alkylene radical, which is part of a 5-, 6- or 7-membered ring.

According to an exemplary embodiment, a method for adhesive bonding a substrate S1 to a substrate S2 is disclosed, comprising:

i) applying a single-component, moisture-curing composition on a substrate S1; and ii) ensuring contact of the applied composition with a substrate S2 within the open time of the composition;

or i') applying a single-component, moisture-curing composition on a substrate S1 and on a substrate S2; and ii') ensuring contact of the applied composition on the substrate S1 with the applied composition on the substrate S2 within the open time of the composition;

wherein the substrate S2 is of the same material as or a different material from a material of the substrate S1.

wherein the single-component, moisture-curing composition is the single-component, moisture-curing composition described herein according to an exemplary aspect.

DETAILED DESCRIPTION

Disclosed are new aldimines that can be used, for example, as latent curing agents in curing compositions, for example, in moisture-curing polyurethane compositions that have isocyanate groups.

It has been found that aldimines according to an exemplary aspect can have advantageous properties. These are compounds that can be liquid at room temperature and, for example, that have hardly any aldehyde odor before, during and after hydrolysis. They can have a long shelf life together with isocyanate groups, for example, also with very reactive aromatic isocyanate groups. For example, during the hydrolysis thereof, an aldehyde can be released, which can be highly compatible in polyurethane compositions, exerts only a slight softening effect there, and exhibits very little tendency to migrate or exude. They therefore can be very well suited as latent curing agents in compositions that have isocyanate groups.

Disclosed is an aldimine of Formula (I),

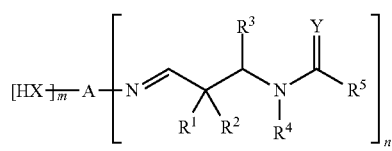

wherein
Y stands for O or S;
A either stands for the radical of an amine after removal of n primary amino groups and m HX groups,
or together with $R^7$ stands for an (n+2*m)-value hydrocarbon radical with 3 to 20 C atoms, which optionally contains at least one heteroatom, for example, in the form of ether-oxygen or tertiary amine-nitrogen;

n stands for 1 or 2 or 3 or 4, and
m stands for 0 or 1 or 2 or 3 or 4,
provided that m+n stands for 2 or 3 or 4 or 5;
$R^1$ and $R^2$ either
independently of one another in each case stand for a monovalent hydrocarbon radical with 1 to 12 C atoms,
or together stand for a divalent hydrocarbon radical with 4 to 12 C atoms, which is part of an optionally substituted, carbocyclic ring with 5 to 8, for example, 6, C atoms;
$R^3$ stands for a hydrogen atom or an alkyl, cycloalkyl, arylalkyl or alkoxycarbonyl radical with 1 to 12 C atoms;
$R^4$ and $R^5$ either
together stand for a divalent radical with 2 to 10 C atoms that optionally has oxygen or sulfur atoms and that is part of an optionally substituted 5- or 6- or 7-membered ring, or $R^4$ stands for an alkyl, cycloalkyl, arylalkyl or acyl radical with 1 to 10 C atoms, and
$R^5$ stands for a hydrogen atom or for a monovalent radical with 1 to 20 C atoms selected from an alkyl, cycloalkyl, arylalkyl, or aryl radical, $-OR^{5'}$, $-SR^{5'}$ and $-NR^{5'}R^{5''}$, wherein $R^{5'}$ and $R^{5''}$ either in each case stand for a hydrocarbon radical or together stand for an alkylene radical, which is part of a 5-, 6- or 7-membered ring;
X stands for O or S or $N-R^6$ or $N-R^7$,
wherein $R^6$
either stands for a monovalent hydrocarbon radical with 1 to 20 C atoms, which optionally has at least one carboxylic acid ester, nitrile, nitro, phosphonic acid ester, sulfone or sulfonic acid ester group, or stands for a substituent of Formula (II),

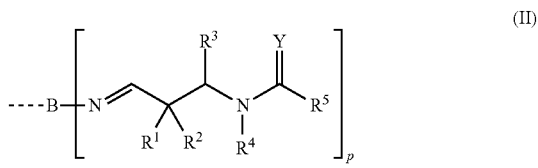

wherein
p stands for 0 or for an integer from 1 to 10,000, and
B stands for a (p+1)-value hydrocarbon radical, which optionally contains ether-oxygen, tertiary amine-nitrogen, hydroxyl groups, secondary amino groups or mercapto groups; and
$R^7$ together with A stands for an (n+2*m)-value hydrocarbon radical with 3 to 20 C atoms, which optionally contains at least one heteroatom, for example, in the form of ether-oxygen or tertiary ine-nitrogen.

In this document, the dotted lines in the formulas in each case represent the bond between a substituent and the related molecule radical.

In this document, the term "primary amino group" includes an amino group in the form of an $NH_2$ group, which is bonded to an organic radical. The term "secondary amino group" includes an amino group in which the nitrogen atom is bonded to two organic radicals, which also can be a common part of a ring. The term "tertiary amino group" includes an amino group in which the nitrogen atom (=tertiary amine-nitrogen) is bonded to three organic radicals, wherein two of these radicals can also be a common part of a ring.

In this document, the term "active hydrogen" includes the hydrogen atom of a hydroxyl, a mercapto or a secondary or primary amino group.

An amine and an isocyanate whose amino and isocyanate groups in each case are bonded exclusively to aliphatic, cycloaliphatic or arylaliphatic radicals are referred to as "aliphatic"; correspondingly, these groups are referred to as aliphatic amino and isocyanate groups.

An amine and an isocyanate, whose amino and isocyanate groups in each case are bonded to an aromatic radical, are referred to as "aromatic"; correspondingly, these groups are referred to as aromatic amino and isocyanate groups.

A "low-odor" substance includes a substance whose odor is perceptible to, i.e., can be smelled by, humans only to a slight extent; it thus does not have an intense odor, such as, for example, formaldehyde, acetaldehyde, isobutyraldehyde, or solvents such as acetone, methyl ethyl ketone or methyl isobutyl ketone, and wherein this slight odor is not considered to be unpleasant or repellent by most humans.

An "odorless" substance includes a substance that most humans cannot smell and that thus has no perceptible odor.

In each case, $R^1$ and $R^2$ can stand for a methyl radical.

$R^3$ can stand for a hydrogen atom.

Y can stand for an oxygen atom.

$R^4$ can stand for a methyl, ethyl, propyl, isopropyl, butyl, 2-ethylhexyl, cyclohexyl or benzyl radical, and $R^5$ can stands for a hydrogen atom or a methyl, ethyl, propyl, isopropyl, butyl, 2-ethylhexyl, cyclohexyl, benzyl, methoxy, ethoxy, propoxy or isopropoxy radical, or $R^4$ and $R^5$ together—with inclusion of the nitrogen atom and the carbonyl or thiocarbonyl group—can form a ring, for example, a 2-pyrrolidone ring, a pyrrolidine-2,5-dione ring, a piperidin-2-one ring, a piperidine-2,6-dione ring, an azepan-2-one ring, an oxazolidin-2-one ring or a thiazolidin-2-one ring, wherein such a ring is optionally substituted.

In an exemplary embodiment of the aldimines of Formula (I), m stands for 1 or 2 or 3 or 4, for example, 1. Such aldimines can have—originating from the HX group—at least one active hydrogen.

Exemplary aldimines of Formula (I) with at least one active hydrogen represent aldimines of Formula (I a),

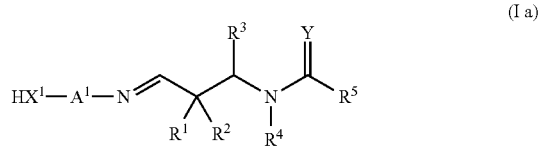

(I a)

wherein
$A^1$ either
stands for a divalent hydrocarbon radical with 2 to 20 C atoms, which optionally contains at least one heteroatom, for example, in the form of ether-oxygen or tertiary amine-nitrogen;
or
together with $R^9$ stands for a trivalent hydrocarbon radical with 3 to 20 C atoms, which optionally contains at least one heteroatom, for example, in the form of ether-oxygen or tertiary amine-nitrogen,
X' stands for O or S or N—$R^8$ or N—$R^9$,
wherein $R^8$
either stands for a monovalent hydrocarbon radical with 1 to 20 C atoms, which optionally has at least one carboxylic acid ester, nitrile, nitro, phosphonic acid ester, sulfone or sulfonic acid ester group, or stands for a substituent of Formula (II a),

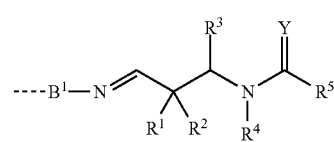

(II a)

whereby $B^1$ stands for a divalent hydrocarbon radical with 2 to 12 C atoms that optionally has ether-oxygen or tertiary amine-nitrogen; and
$R^9$ together with $A^1$ stands for a trivalent hydrocarbon radical with 3 to 20 C atoms, which optionally contains at least one heteroatom, for example, in the form of ether-oxygen or tertiary amine-nitrogen,
and Y, $R^1$, $R^2$, $R^3$, $R^4$ and $R^5$ have the already mentioned meanings, provided that $A^1$ does not have any active hydrogen.

In an exemplary embodiment of the aldimines of Formula (I), m stands for zero, and n stands for 2, or 3 or 4. Such aldimines represent polyaldimines. In this document, substance names beginning with "poly," such as polyaldimine, polyamine or polyisocyanate, include substances that formally contain two or more of the functional groups per molecule that occur in their name Exemplary aldimines of Formula (I) with m=0 represent aldimines of Formula (I b),

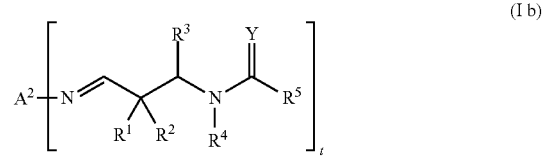

(I b)

wherein
t stands for 2 or 3;
$A^2$ stands for the radical of an amine B2 after removal of t primary amino groups,
and Y, $R^1$, $R^2$, $R^3$, $R^4$ and $R^5$ have the already mentioned meanings, provided that the aldimine of Formula (I b) does not have any active hydrogen.

Aldimines of Formula (I) can be made available from the reaction of at least one amine B of Formula (III) with at least one aldehyde ALD of Formula (IV),

(III)

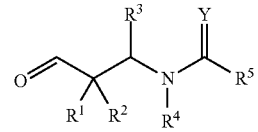

(IV)

wherein
$X^a$ stands for O or S or N—$R^{6a}$ or N—$R^7$,
whereby $R^{6a}$ either stands for a monovalent hydrocarbon radical with 1 to 20 C atoms, which optionally has at least one carboxylic acid ester, nitrile, nitro, phosphonic acid ester, sulfone or sulfonic acid ester group, or for a substituent of Formula (III'),

(III')

and m, n, A, B, Y, $R^1$, $R^2$, $R^3$, $R^4$, $R^5$ and p have the already mentioned meanings.

The reaction between an amine B of Formula (III) and an aldehyde ALD of Formula (IV) can be carried out in a condensation reaction, with water being separated off. Exemplary condensation reactions are described, for example, in Houben-Weyl, "Methoden der organischen Chemie [Methods of Organic Chemistry]," Vol. XI/2, page 73ff. In this connection, the aldehyde ALD can be used stoichiometrically or in stoichiometric excess relative to the primary amino groups of amine B. Such condensation reactions can be performed in the presence of a solvent, by means of which the water that is produced in the reaction is removed azeotropically. For the production of the aldimines of Formula (I), however, a production method without using solvents can be used, wherein the water that is formed during the condensation is removed directly from the reaction mixture by applying a vacuum. In such case, because of the solvent-free production, distilling-off of the solvent after production is completely unnecessary, which simplifies the production process. Moreover, the aldimine is thus free of solvent residues, which could cause an objectionable odor.

As amine B of Formula (III), in an exemplary embodiment, compounds are suitable that—in addition to one or more primary amino groups—have at least one reactive group, carrying an active hydrogen, in the form of a hydroxyl, mercapto or secondary amino group. Examples of such amines B with more than one active hydrogen-carrying reactive group are More than one secondary amino group and one or more aliphatic amines that carry primary amino groups such as, for example, N,N'-bis-(3-amino-propyl)ethylenediamine, triethylenetetramine (TETA), tetraethylenepentamine (TEPA), pentaethylenehexamine and higher homologs of linear polyethylenamines, N,N'-bis-(3-aminopropyl)-ethylenediamine, products from repeated cyanoethylation or cyanobutylation and subsequent hydrogenation of primary di- and polyamines with several primary amino groups, such as, for example, N,N'-bis-(3-aminopropyl)-ethylenediamine, N,N'-bis-(3-aminopropyl)-1,4-diaminobutane, N,N'-bis-(3-aminopropyl)-2-methyl-1,5-pentanediamine, N,N'-bis-(3-amino-1-ethylpropyl)-2-methyl-1,5-pentanediamine as well as polyethylenimines of different degrees of polymerization (molar-mass range of 500 to 1,000,000 g/mol), as they are available, for example, under the trade name Lupasol® by BASF in pure form or as aqueous solutions, whereby these polyethylenimines—in addition to primary and secondary amino groups—also contain tertiary amino groups;

More than one hydroxyl group and one or more hydroxyamines that carry primary amino groups, for example, derivatives of polyalkoxylated trivalent or higher-value alcohols or of polyalkoxylated polyamines, as well as amino sugars, for example glucosamine or galactosamine;

At least one hydroxyl-carrying hydroxypolyamine and at least one secondary amino-group-carrying hydroxypolyamine from cyanoethylation or cyanobutylation and subsequent hydrogenation of hydroxyamines such as, for example, N-hydroxyethyl-1,2-ethanediamine, N-hydroxypropyl-1,2-ethanediamine, N-hydroxyethyl-1,3-propanediamine, and N3-hydroxyethyl-1,3-pentanediamine.

As amine B of Formula (III) for reaction with an aldehyde ALD of Formula (IV), amines B1 of Formula (III a) can be used, $$HX^{1a}\text{-}A^1\text{-}NH_2 \qquad \text{(III a)}$$

wherein $X^{1a}$ stands for O or S or N—$R^{8a}$ or N—$R^9$, wherein $R^{8a}$ either stands for a monovalent hydrocarbon radical with 1 to 20 C atoms, which optionally has at least one carboxylic acid ester, nitrile, nitro, phosphonic acid ester, sulfone or sulfonic acid ester group, or stands for a substituent of Formula (III a'), $$\text{—}B^1\text{—}NH_2 \qquad \text{(III a')}$$

and $A^1$, $B^1$ and $R^9$ have the already mentioned meanings.

An aldimine of Formula (I a) can be obtained from the reaction of at least one amine B1 of Formula (III a) with at least one aldehyde ALD of Formula (IV).

Examples of amines B1 include

Compounds with one or two primary aliphatic groups and one secondary amino group, such as, for example, N-methyl-1,2-ethanediamine, N-ethyl-1,2-ethanediamine, N-butyl-1,2-ethanediamine, N-hexyl-1,2-ethanediamine, N-(2-ethylhexyl)-1,2-ethanediamine, N-cyclohexyl-1,2-ethanediamine, 4-aminomethyl-piperidine, 3-(4-aminobutyl)-piperidine, N-(2-aminoethyl) piperazine, diethylenetriamine (DETA), bis-hexamethylenetriamine (BHMT), 3-(2-aminoethyl) aminopropylamine; di- and triamines from the cyanoethylation or cyanobutylation and subsequent hydrogenation of primary mono- and diamines, for example N-methyl-1,3-propanediamine, N-ethyl-1,3-propanediamine, N-butyl-1,3-propanediamine, N-hexyl-1,3-propanediamine, N-(2-ethylhexyl)-1,3-propanediamine, N-dodecyl-1,3-propanediamine, N-cyclohexyl-1,3-propanediamine, 3-methylamino-1-pentylamine, 3-ethylamino-1-pentylamine, 3-butylamino-1-pentylamine, 3-hexylamino-1-pentylamine, 3-(2-ethylhexyl)amino-1-pentylamine, 3-dodecylamino-1-pentylamine, 3-cyclohexylamino-1-pentylamine, dipropylenetriamine (DPTA), N3-(3-aminopentyl)-1,3-pentanediamine, N5-(3-aminopropyl)-2-methyl-1,5-pentanediamine, N5-(3-amino-1-ethylpropyl)-2-methyl-1,5-pentanediamine, and fatty diamines such as N-cocoalkyl-1,3-propanediamine, N-oleyl-1,3-propanediamine, N-soya alkyl-1,3-propanediamine, N-tallowalkyl-1,3-propanediamine or N—($C_{16\text{-}22}$-alkyl)-1,3-propanediamine, as they are available, for example, under the trade name Duomeen® by Akzo Nobel; the products from the Michael addition of aliphatic primary di- or triamines with acrylonitrile, maleic- or fumaric acid diesters, citraconic acid diesters, acrylic- and methacrylic acid esters, acrylic and methacrylic acid amides, and itaconic acid diesters, reacted at a molar ratio of 1:1;

Hydroxyamines, such as, for example, 2-aminoethanol, 2-amino-1-propanol, 1-amino-2-propanol, 3-amino-1-propanol, 4-amino-1-butanol, 4-amino-2-butanol, 2-amino-2-methylpropanol, 5-amino-1-pentanol, 6-amino-1-hexanol, 7-amino-1-heptanol, 8-amino-1-octanol, 10-amino-1-decanol, 12-amino-1-dodecanol, 4-(2-aminoethyl)-2-hydroxyethylbenzene, 3-aminomethyl-3,5,5-trimethyl-cyclohexanol; derivatives of glycols carrying a primary amino group, such as diethylene glycol, dipropylene glycol, dibutylene glycol and higher oligomers and polymers of these glycols, for example 2-(2-aminoethoxy)-ethanol, 2-(2-(2-aminoethoxy)ethoxy)ethanol, α-(2-hydroxymethylethyl)-ω-(2-amino-methylethoxy)-poly(oxy(methyl-1,2-ethanediyl)); a hydroxyl group and derivatives of polyalkyoxylated trivalent or higher-value alcohols carrying a primary amino group; products from simple cyanoethylation and subsequent hydrogenation of glycols, for example 3-(2-hydroxyethoxy)-propylamine, 3-(2-(2-hydroxyethoxy)-ethoxy)-propylamine and 3-(6-hydroxyhexyloxy)-propylamine;

Mercaptoamines, such as, for example, 2-aminoethanethiol (cysteamine), 3-aminopropanethiol, 4-amino-1-butanethiol, 6-amino-1-hexanethiol, 8-amino-1-octanethiol, 10-amino-1-decanethiol and 12-amino-1-dodecanethiol.

As amine B1, the following can be used: N-methyl-1,2-ethanediamine, N-ethyl-1,2-ethanediamine, N-cyclohexyl-1,2-ethanediamine, N-methyl-1,3-propanediamine, N-ethyl-1,3-propanediamine, N-butyl-1,3-propanediamine, N-cyclohexyl-1,3-propanediamine, 4-aminomethyl-piperidine, 3-(4-aminobutyl)-piperidine, DETA, DPTA, BHMT and fatty diamines such as, for example, N-cocoalkyl-1,3-propanediamine, N-oleyl-1,3-propanediamine, N-soya alkyl-1,3-propanediamine, and N-tallowalkyl-1,3-propanediamine; products from the Michael addition reaction of aliphatic primary diamines with maleic and fumaric acid diesters, acrylic and methacrylic acid esters, acrylic and methacrylic acid amides, for example, with maleic acid diesters, for example, maleic acid dimethyl-, -diethyl-, -dipropyl- and -dibutylester, and with acrylic acid esters, for example, acrylic acid methyl ester, reacted at a molar ratio of 1:1; as well as aliphatic hydroxy- or mercaptoamines, in which the primary amino group is separated from the hydroxyl or mercapto group by a chain of at least 5 atoms, or by a ring, for example, 5-amino-1-pentanol, 6-amino-1-hexanol and higher homologs thereof, 4-(2-aminoethyl)-2-hydroxyethylbenzene, 3-aminomethyl-3,5,5-trimethyl-cyclohexanol, 2-(2-aminoethoxy)-ethanol, triethylene glycol monoamine and higher oligomers and polymers thereof, 3-(2-hydroxyethoxy)-propylamine, 3-(2-(2-hydroxyethoxy)-ethoxy)-propylamine and 3-(6-hydroxy-hexyloxy)-propylamine.

As amine B1, exemplary amines can be selected from N-methyl-1,2-ethanediamine, N-ethyl-1,2-ethanediamine, N-cyclohexyl-1,2-ethanediamine, N-methyl-1,3-propanediamine, N-ethyl-1,3-propanediamine, N-butyl-1,3-propanediamine, N-cyclohexyl-1,3-propanediamine, 4-aminomethyl-piperidine, 3-(4-aminobutyl)-piperidine, DETA, DPTA, BHMT, fatty diamines, for example, N-cocoalkyl-1,3-propanediamine, N-oleyl-1,3-propanediamine, N-soya alkyl-1,3-propanediamine and N-tallowalkyl-1,3-propanediamine; 5-amino-1-pentanol, 6-amino-1-hexanol, 4-(2-aminoethyl)-2-hydroxyethylbenzene, 3-aminomethyl-3,5,5-trimethyl-cyclohexanol, 2-(2-aminoethoxy)-ethanol, triethylene glycol monoamine, 3-(2-hydroxyethoxy)-propylamine, 3-(2-(2-hydroxyethoxy)-ethoxy)-propylamine and 3-(6-hydroxyhexyloxy)-propylamine.

As amine B1, exemplary amines can be selected from 5-amino-1-pentanol, 6-amino-1-hexanol, 4-(2-aminoethyl)-2-hydroxyethylbenzene, 3-aminomethyl-3,5,5-trimethyl-cyclohexanol, 2-(2-aminoethoxy)-ethanol, triethylene-glycol monoamine, 3-(2-hydroxyethoxy)-propylamine, 3-(2-(2-hydroxyethoxy)-ethoxy)-propylamine and 3-(6-hydroxyhexyloxy)-propylamine.

As amine B of Formula (III) for reaction with an aldehyde ALD of Formula (IV), amines B2 of Formula (III b),

  (III b)

wherein $A^2$ and t have the already mentioned meanings, can be used.

An aldimine of Formula (I b) can be obtained from the reaction of at least one amine B2 of Formula (III b) with at least one aldehyde ALD of Formula (IV).

Examples of amines B2 include

Aliphatic, cycloaliphatic or arylaliphatic diamines, for example ethylene diamine, 1,2-propanediamine, 1,3-propanediamine, 2-methyl-1,2-propanediamine, 2,2-dimethyl-1,3-propanediamine, 1,3-butanediamine, 1,4-butanediamine, 1,3-pentanediamine (DAMP), 1,5-pentanediamine, 1,5-diamino-2-methylpentane (MPMD), 2-butyl-2-ethyl-1,5-pentanediamine (C11-neodiamine), 1,6-hexanediamine, 2,5-dimethyl-1,6-hexanediamine, 2,2,4- and 2,4,4-trimethylhexamethylenediamine (TMD), 1,7-heptanediamine, 1,8-octanediamine, 1,9-nonanediamine, 1,10-decanediamine, 1,11-undecanediamine, 1,12-dodecanediamine, 1,2-, 1,3- and 1,4-diaminocyclohexane, bis-(4-aminocyclohexyl)-methane ($H_{12}$-MDA), bis-(4-amino-3-methylcyclohexyl)-methane, bis-(4-amino-3-ethylcyclohexyl)-methane, bis-(4-amino-3,5-dimethylcyclohexyl)-methane, bis-(4-amino-3-ethyl-5-methylcyclohexyl)-methane (M-MECA), 1-amino-3-aminomethyl-3,5,5-trimethylcyclohexane (=isophorone diamine or IPDA), 2- and 4-methyl-1,3-diaminocyclohexane and mixtures thereof, 1,3- and 1,4-bis-(aminomethyl)cyclohexane, 2,5(2,6)-bis-(aminomethyl)-bicyclo[2.2.1]heptane (NBDA), 3(4),8(9)-bis-(aminomethyl)-tricyclo-[5.2.1.0$^{2,6}$]decane, 1,4-diamino-2,2,6-trimethylcyclohexane (TMCDA), 1,8-menthanediamine, 3,9-bis-(3-aminopropyl)-2,4,8,10-tetraoxaspiro[5.5]-undecane as well as 1,3- and 1,4-xylylenediamine;

Ether-group-containing aliphatic diamines, for example bis-(2-aminoethyl)ether, 3,6-dioxaoctane-1,8-diamine, 4,7-dioxadecane-1,10-diamine, 4,7-dioxadecane-2,9-diamine, 4,9-dioxadodecane-1,12-diamine, 5,8-dioxadodecane-3,10-diamine and higher oligomers of these diamines, bis-(3-aminopropyl)polytetrahydrofurans and other polytetrahydrofuran-diamines with molecular weights in the range of, for example, 350 to 5200, as well as polyoxyalkylene-diamines. The latter can represent products from the amination of polyoxyalkylene diols and are available, for example, under the name Jeffamine® (by Huntsman), under the name polyetheramine (by BASF) or under the name PC Amine® (by Nitroil). Exemplary polyoxyalkylene-diamines include Jeffamine® D-230, Jeffamine® D-400, Jeffamine® D-2000, Jeffamine® D-4000, Jeffamine® XTJ-511, Jeffamine® ED-600, Jeffamine® ED-900, Jeffamine® ED-2003, Jeffamine® XTJ-568, Jeffamine® XTJ-569, Jeffamine® XTJ-523, Jeffamine® XTJ-536, Jeffamine® XTJ-542, Jeffamine® XTJ-559, Jeffamine® EDR-104, Jeffamine® EDR-148, Jeffamine® EDR-176; polyetheramine D 230, polyetheramine D 400 and polyetheramine D 2000, PC Amine® DA 250, PC Amine® DA 400, PC Amine® DA 650 and PC Amine® DA 2000;

Aliphatic, cycloaliphatic or arylaliphatic triamines such as, for example, 4-aminomethyl-1,8-octanediamine, 1,3,5-tris-(aminomethyl)-benzene, 1,3,5-tris-(aminomethyl)-cyclohexane, tris-(2-aminoethyl)-amine, tris-(2-aminopropyl)-amine, tris-(3-aminopropyl)-amine;

Polyoxyalkylene-triamines, which can represent products from the amination of polyoxyalkylene-triols and are available, for example, under the trade name Jeffamine® (by Huntsman), under the name polyetheramine (by BASF) or under the name PC Amine® (by Nitroil), such as, for example, Jeffamine® T-403, Jeffamine® T-3000, Jeffamine® T-5000; polyetheramine T403, polyetheramine T5000; and PC Amine® TA 403, and PC Amine® TA 5000.

Aromatic di- and triamines, such as, for example, 1,2-, 1,3- and 1,4-phenylenediamine, 2,4- and 2,6-toluoylenediamine (TDA), 3,4-toluoylenediamine, 3,5-dimethylthio-2,4- and -2,6-toluoylenediamine, 3,5-diethyl-2,4- and -2,6-toluoylenediamine (DETDA), 2,4,6-triethyl-1,3-phenylenediamine, 2,4,6-triisopropyl-1,3-phenylenediamine, 3-ethyl-5-methyl-2,4-toluoylenediamine, 3,5-diisopropyl-2,4-toluoylenediamine, 3,5-bis-(1-methylpropyl)-2,4-toluoylenediamine, 3,5-bis-(tert-butyl)-2,4-toluylenediamine, 3-ethyl-5-isopropyl-2,4-toluoylenediamine, 5-isopropyl-2,4-toluoylenediamine, 5-(tert-butyl)-2,4-toluoylenediamine, 4,6-bis-(1-methylpropyl)-1,3-phenylenediamine, 4-isopropyl-6-(tert-butyl)-1,3-phenylenediamine, 4-ethyl-6-isopropyl-1,3-phenylenediamine, 4-ethyl-6-(2-methylpropyl)-1,3-phenylenediamine, 4-ethyl-6-(1-methylpropyl)-1,3-phenylenediamine, 4-ethyl-6-(2-methylpropyl)-1,3-phenylenediamine, 4-isopropyl-6-(1-methylpropyl)-1,3-phenylenediamine, 4-(tert-butyl)-6-(2-methylpropyl)-1,3-phenylenediamine, 4-cyclopentyl-6-ethyl-1,3-phenylenediamine, 4-cyclopentyl-6-isopropyl-1,3-phenylenediamine, 4,6-dicyclopentyl-1,3-phenylenediamine, 3-isopropyl-2,6-toluoylenediamine, 2-methylpropyl-(4-chloro-3,5-diaminobenzoate), tert-butyl-(4-chloro-3,5-diaminobenzoate), 2,6-diaminopyridine, melamine, 4,4'-, 2,4'- and 2,2'-diaminodiphenylmethane (MDA), 3,3'-dimethyl-4,4'-diaminodiphenylmethane, 3,3'-dichloro-4,4'-diaminodiphenylmethane (MOCA), 3,3',5,5'-tetraethyl-4,4'-diaminodiphenylmethane (M-DEA), 3,3',5,5'-tetraethyl-2,2'-dichloro-4,4'-diaminodiphenylmethane (M-CDEA), 3,3'-diisopropyl-5,5'-dimethyl-4,4'-diaminodiphenylmethane (M-MIPA), 3,3',5,5'-tetraisopropyl-4,4'-diaminodiphenylmethane (M-DIPA), 3,3',5,5'-tetra-(1-methylpropyl)-4,4'-diaminodiphenylmethane, 3,3'-dimethyl-5,5'-di-tert-butyl-4,4'-diaminodiphenylmethane, 3,3'-di-tert-butyl-4,4'-diaminodiphenylmethane, 4,4'-diaminodiphenylsulfone (DDS), 4-amino-N-(4-aminophenyl)-benzenesulfonamide, 5,5'-methylenedianthranilic acid, dimethyl-(5,5'-methylenedianthranilate), 1,3-propylene-bis-(4-aminobenzoate), 1,4-butylene-bis-(4-aminobenzoate), polytetramethylene oxide-bis-(4-aminobenzoate) (available as Versalink® by Air Products) and 1,2-bis-(2-aminophenylthio)-ethane.

Polyamines with primary aromatic amino groups and primary aliphatic amino groups, such as, for example, 4-aminoethylaniline, 4-aminomethylaniline, 4-[(4-aminocyclohexyl)methyl]aniline, 2-aminoethylaniline, 2-aminomethylaniline, 2-[(4-aminocyclohexyl)methyl]aniline and 4-[(2-aminocyclohexyl)methyl]aniline.

The amine B2 can be selected from 1,6-hexamethylenediamine, MPMD, DAMP, IPDA, TMD, 1,3-xylylenediamine, 1,3-bis-(aminomethyl)cyclohexane, bis-(4-aminocyclohexyl)-methane, bis-(4-amino-3-methylcyclohexyl)-methane, 3(4),8(9)-bis-(aminomethyl)-tricyclo[5.2.1.0$^{2,6}$]decane, 1,2-, 1,3- and 1,4-diaminocyclohexane, 1,4-diamino-2,2,6-trimethylcyclohexane, 3,6-dioxaoctane-1,8-diamine, 4,7-dioxadecane-1,10-diamine, 4-aminomethyl-1,8-octanediamine, polyoxyalkylene polyamines with two or three amino groups, for example, the types D-230, D-400, D-2000, T-403 and T-5000 by Huntsman that are available under the trade name Jeffamine® and compounds by BASF or Nitroil that are analogous to this; 1,3- and 1,4-phenylenediamine, 2,4- and 2,6-toluoylenediamine, 4,4'-, 2,4'- and 2,2'-diaminodiphenylmethane, 3,3'-dichloro-4,4'-diaminodiphenylmethane and mixtures of the above-mentioned polyamines.

In addition, at least one aldehyde ALD of Formula (IV) can be used for the production of an aldimine of Formula (I),

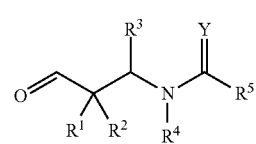

(IV)

wherein Y, $R^1$, $R^2$, $R^3$, $R^4$ and $R^5$ have the already mentioned meanings.

In an exemplary embodiment, an aldehyde ALD of Formula (IV) can be available as a product of an α-aminoalkylation that is analogous to the Mannich reaction, as is known from technical literature. In this case, an aldehyde Y1 of Formula (V), an aldehyde Y2 of Formula (VI), and a compound C of Formula (VII) can be reacted, with water being separated off, to form an aldehyde ALD of Formula (IV).

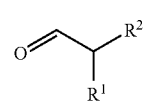

(V)

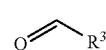

(VI)

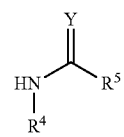

(VII)

In Formulas (V), (VI) and (VII), Y, $R^1$, $R^2$, $R^3$ and $R^4$ have the already mentioned meanings.

This reaction can be run, for example, either with the free reagents Y1, Y2 and C according to Formulas (V), (VI) and (VII), or the reagents can be used partially or completely in derivatized form. In an exemplary embodiment, the reaction with all reagents in free form is run as a single-pot reaction, and after the reaction is completed, the aldehyde ALD is purified by distillation. In an exemplary embodiment, organic solvents are not used.

As aldehyde Y1 of Formula (V), the following aldehydes can be used: isobutyraldehyde, 2-methylbutyraldehyde, 2-ethylbutyraldehyde, 2-methylvaleraldehyde, 2-ethylcapronaldehyde, cyclopentanecarboxaldehyde, cyclohexanecarboxaldehyde, 1,2,3,6-tetrahydrobenzaldehyde, 2-methyl-3-phenylpropionaldehyde, 2-phenylpropionaldehyde and diphenylacetaldehyde. Isobutyraldehyde can be used.

As aldehyde Y2 of Formula (VI), especially the following aldehydes can be used: formaldehyde, acetaldehyde, propionaldehyde, butyraldehyde, isobutyraldehyde, phenylacetaldehyde and glyoxylic acid ester, for example, glyoxylic acid ethyl ester. Formaldehyde can be used.

As compound C of Formula (VII), on the one hand amides can be used, for example, N-methylformamide, N-ethylformamide, N-butylformamide, N-methylacetamide, N-ethylacetamide, N-isopropylacetamide, N-butylacetamide, N—N-(2-ethylhexyl)acetamide, cyclohexylacetamide, N-benzylacetamide, N-methylpropionamide, N-methyl-butyramide, N-methyl-2-ethylcapronamide, N-methyl-benzamide; in addition, lactams and derivatives thereof, for example, 2-pyrrolidone, 5-methyl-2-pyrrolidone, piperidin-2-one, ε-caprolactam, 2-azabicyclo[2.2.1]hept-5-en-3-one; in addition, carbamates mono-substituted on a nitrogen atom and derivatives thereof, for example, O-ethyl-N-methylcarbamate, O-ethyl-N-ethylcarbamate, O-ethyl-N-propylcarbamate, O-methyl-N-ethylcarbamate, O-methyl-N-propylcarbamate, O-methyl-N-butylcarbamate, acetylurethane, N-butylurethane, oxazolidin-2-one, oxazolidine-2,5-dione; in addition, imides and derivatives thereof, for example, pyrrolidine-2,5-dione (=succinic acid imide), 3,4-dimethyl-pyrrolidine-2,5-dione, 3,3,4,4-tetramethyl-pyrrolidine-2,5-dione, 3-ethyl-3-methyl-pyrrolidine-2,5-dione, piperidine-2,6-dione, 4,4-dimethyl-piperidine-2,6-dione, 1,5,5-trimethylimidazolidine-2,4-dione, phthalimide, methylphthalimide, hexahydrophthalimide, methylhexahydrophthalimide, 5,5-dimethyl-1,3-oxazolidine-2,4-dione, acetimide; in addition, substances that are analogous to the above-mentioned compounds with sulfur atoms instead of oxygen atoms, for example, N-methyl thioacetamide, N-butyl thioacetamide, N-(2-ethylhexyl)thioacetamide, N-benzyl thioacetamide, N-methyl butyl thioamide, N-methyl-(2-ethyl capron thioamide), N-methylbenz thioamide, 2-thiopyrrolidone, O-ethyl-N-methyl-thiocarbamate, S-ethyl-N-methyl-thiocarbamate, O-methyl-N-ethyl-thiocarbamate, thiazolidin-2-one and thiazolidine-2,5-dione.

The compound C can be selected from N-methylformamide, N-methylacetamide, N-butylacetamide, N-(2-ethylhexyl)acetamide, N-benzylacetamide, N-methylbutyramide, N-methyl-(2-ethylcapronamide), N-methylbenzamide, O-ethyl-N-methylcarbamate, 2-pyrrolidone, piperidin-2-one, ε-caprolactam, oxazolidin-2-one, thiazolidin-2-one, pyrrolidine-2,5-dione and phthalimide.

In an exemplary embodiment, an aldehyde ALD of Formula (IV) can be available starting from an intermediate product ZW1 of Formula (VIII).

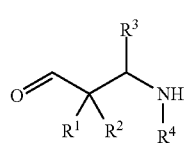

(VIII)

In Formula (VIII), $R^1$, $R^2$, $R^3$ and $R^4$ have the already mentioned meanings.

The intermediate product ZW1 of Formula (VIII) is also available as a product of α-aminoalkylation that is analogous to the Mannich reaction in the same way as previously described for the aldehyde ALD, starting from the already mentioned aldehydes Y1 and Y2, whereby instead of the compound C of Formula (VII), however, a primary amine of Formula $R^4$—$NH_2$ can be used, wherein $R^4$ has the already mentioned meaning, and wherein the aldehydes Y1 and Y2 and the primary amine are used approximately at a molar ratio of 1:1:1. As a primary amine for the production of an intermediate product ZW1, the following are suitable: for example, primary aliphatic amines, for example, methylamine, ethylamine, propylamine, isopropylamine, butylamine, isobutylamine, sec-butylamine, hexylamine, cyclohexylamine, octylamine, 2-ethyl-1-hexylamine, benzylamine, 1- or 2-phenylethylamine and decylamine.

For the production of an aldehyde ALD of Formula (IV), the intermediate product ZW1 can then be reacted with a carboxylic acid, for example, in the form of a carboxylic acid chloride, -ester, or -anhydride, to form the corresponding amide, wherein saturated aliphatic or cycloaliphatic carboxylic acids are suitable as carboxylic acid, such as, for example, formic acid, acetic acid, propionic acid, butyric acid, isobutyric acid, valeric acid, isovaleric acid, pivalic acid, caproic acid, cyclohexanecarboxylic acid, enanthic acid, caprylic acid, 2-ethylhexanoic acid, pelargonic acid, capric acid, neodecanoic acid, undecanoic acid, lauric acid, tridecanoic acid, myristic acid, pentadecanoic acid, palmitic acid, margaric acid, stearic acid, isostearic acid, and arachidic acid; singly or multiply unsaturated aliphatic carboxylic acids such as, for example, palmitoleic acid, oleic acid, erucic acid, sorbic acid, linoleic acid, linolenic acid, eleostearic acid, ricinoleic acid, and ricinenic acid; aromatic carboxylic acids, such as, for example, benzoic acid and the positional-isomeric toluic acids, methoxybenzoic acids and nitrobenzoic acids; as well as chlorides, esters and anhydrides of the above-mentioned carboxylic acids; as well as in addition anhydrides of dicarboxylic acids such as phthalic acid anhydride, 4-methylphthalic acid anhydride, succinic acid anhydride, maleic acid anhydride, citraconic acid anhydride, hexahydrophthalic acid anhydride, 4-methylhexahydrophthalic acid anhydride, and 1,2,3,6-tetrahydrophthalic acid anhydride.

In addition, for the production of an aldehyde ALD of Formula (IV), the intermediate product ZW1 can be reacted with a carbonate or, for example, a chloroformic acid ester, such as, for example, methyl-, ethyl-, propyl-, isopropyl-, butyl-, isobutyl-, neopentyl-, hexyl-, octyl-, 2-ethylhexyl-, benzyl-, phenyl-, tolyl- and methoxyphenyl-chloroformate, to form the corresponding urethane.

In addition, for the production of an aldehyde ALD of Formula (IV), the intermediate product ZW1 can be reacted with an N,N-disubstituted carbamate or an N,N-disubstituted carbamic acid chloride, such as, for example, N,N-dimethyl-, N,N-diethyl-, N,N-diisopropyl-, N,N-dibutyl-, N-methyl-N-phenyl-, and N,N-diphenyl-carbamoyl chloride, as well as, for example, 1-pyrrolidine-, 1-piperidine-, 1-morpholine- and 4-methyl-1-piperazine-carbonyl chloride, to form the corresponding urea.

In addition, for the production of an aldehyde ALD of Formula (IV), the intermediate product ZW1 can be reacted with a thiocarboxylic acid, such as, for example, thioacetic acid, thiopropionic acid, thiobenzoic acid, thiotoluic acid or phenylthioacetic acid, for example, in the form of an acid chloride, -ester or -anhydride, to form the corresponding thioamide.

In addition, for the production of an aldehyde ALD of Formula (IV), the intermediate product ZW1 can be reacted with a (di)thiocarbonate, a chloro(di)thioformic acid ester, an N,N-disubstituted thiocarbamate or an N,N-di-substituted carbamic acid chloride, such as, for example, O-methyl-, O-ethyl-, O-phenyl- or O-p-tolyl-chloridothiocarbonate, S-methyl-, S-ethyl-, S-propyl- or S-phenyl-chloridothiocarbonate, phenyl chlorididothiocarbonate, N,N-dimethyl-, N,N-diethyl-, N-methyl-N-phenyl-, or N,N-diphenyl-thiocarbamoyl chloride, to form the corresponding (di)thiourethane or -urea.

The reaction of an aldehyde Y1 of Formula (V), as it was already mentioned above, with a compound of Formula (IX) offers another possibility for the production of an aldehyde ALD of Formula (IV)

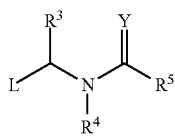
(IX)

wherein

L stands for a radical, selected from a halogen atom,
an alkoxy group, a carboxylic acid ester group, a urethane group that is bonded via the nitrogen, a dialkylamino group, and a di- or trialkylammonium group,
and Y, $R^3$, $R^4$ and $R^5$ have the already described meanings.

As a compound of Formula (IX), the following can be used: N-chloro- or N-bromomethyl-N-alkyl-carbamates such as, for example, N-chloromethyl-N-methyl-carbamic acid ethyl ester, as well as N-bromomethyl-imides such as, for example, N-bromomethyl-phthalimide and N-bromomethyl-pyrrolidine-2,5-dione.

The aldehydes ALD of Formula (IV) can have a series of special properties. Because of their chemical structure, they can have no or only a slight amine-like odor even at relatively low molecular weight. They can be low-odor or odorless. In addition, in α-position on the carbonyl-C atom, they have no hydrogen atom. As a result, for example, their aldehyde groups cannot tautomerize to form enol groups and are thus unreactive to isocyanate groups. In addition, in contrast to β-amino aldehydes, they are not basic; this gives them—together with isocyanate groups—an especially long shelf life, for example, also together with aromatic isocyanate groups. In addition, besides the aldehyde group, they have additional functional groups that are capable of forming hydrogen bridge bonds. This is possibly one of the reasons why they are highly compatible in plastic compositions forming hydrogen bridges, for example, in polyurethane compositions. They do not tend to migrate or exude there and have only a slight softening effect, which is often very advantageous.

The aldehyde ALD of Formula (IV) can be selected from N-(2,2-dimethyl-3-oxopropyl)-N-methylformamide, N-(2,2-dimethyl-3-oxopropyl)-N-methylacetamide, N-(2,2-dimethyl-3-oxopropyl)-N-butylacetamide, N-(2,2-dimethyl-3-oxopropyl)-N-(2-ethylhexyl)acetamide, N-(2,2-dimethyl-3-oxopropyl)-N-benzylacetamide, N-(2,2-dimethyl-3-oxopropyl)-N-methylbutyramide, N-(2,2-dimethyl-3-oxopropyl)-N-methyl-(2-ethylcapronamide), N-(2,2-dimethyl-3-oxopropyl)-N-methylbenzamide, O-ethyl-N-(2,2-dimethyl-3-oxopropyl)-N-methylcarbamate, N-(2,2-dimethyl-3-oxopropyl)-pyrrolidin-2-one, N-(2,2-dimethyl-3-oxopropyl)-piperidin-2-one, N-(2,2-dimethyl-3-oxopropyl)-azepan-2-one, N-(2,2-dimethyl-3-oxopropyl)-oxazolidin-2-one, N-(2,2-dimethyl-3-oxopropyl)-thiazolidin-2-one, N-(2,2-dimethyl-3-oxopropyl)-pyrrolidine-2,5-dione and N-(2,2-dimethyl-3-oxopropyl)-phthalimide.

Exemplary aldimines of Formula (I), include those obtained from the reaction of either at least one amine B1 of Formula (III a) or at least one amine B2 of Formula (III b) and at least one of the above-mentioned, exemplary aldehydes ALD of Formula (IV).

Another exemplary way to obtain an aldimine of Formula (I) starts with an intermediate product ZW2 of Formula (X),

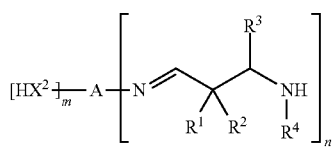
(X)

wherein
$X^2$ stands for O or S,
and m, n, A, $R^1$, $R^2$, $R^3$ and $R^4$ have the already mentioned meanings.

For the production of an aldimine of Formula (I), the intermediate product ZW2—instead of the intermediate product ZW1 of Formula (VIII)—can be reacted either with at least one carboxylic acid or thiocarboxylic acid, for example, in the form of a carboxylic or thiocarboxylic acid chloride, -ester or -anhydride, to form the corresponding amide or thioamide, or with at least one carbonate or thiocarbonate, for example, in the form of a chloroformic acid or chlorothioformic acid ester, to form the corresponding urethane or thiourethane, wherein the same carboxylic acids or thiocarboxylic acids and carbonates or thiocarbonates are suitable as already described in the reaction with an intermediate product ZW1.

The intermediate product ZW2 can be obtained, for example, by the reaction of a corresponding intermediate product ZW1 with at least one amine B of Formula (III) at a suitable ratio, wherein amines B with secondary amino groups are, for example, not suitable. Suitable for this reaction are, for example, the above-mentioned amines B2 and the above-mentioned amines B1, in which $X^{1a}$ stands for O or S, for example, for O.

The embodiments of aldimines of Formula (I), which have at least one group HX, can optionally be in equilibrium with cyclic forms, as they are shown in Formula (XI) by way of example for aldimines of Formula (I) with m=1. In the case of aminoaldimines, these cyclic forms can be cyclic aminals, for example imidazolidines or tetrahydropyrimidines; in the case of hydroxyaldimines, they can be cyclic aminoacetals, for example, oxazolidines or tetrahydrooxazines; and in the case of mercaptoaldimines, they can be cyclic thioaminals, for example, thiazolidines or tetrahydrothiazines.

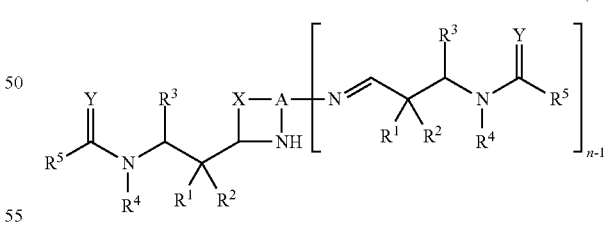
(XI)

In the Formula (XI), n, A, $R^1$, $R^2$, $R^3$, $R^4$, $R^5$, X and Y have the already mentioned meanings.

In an exemplary embodiment, some aldimines of Formula (I) that contain HX groups do not, for example, tend toward cyclization. For example, for aminoaldimines, it can be shown by means of IR and NMR-spectroscopic methods that these compounds can be present predominantly in the open-chain, i.e., the aldimine form, while the cyclic form, i.e., the aminal form, does not occur or occurs only in trace amounts. Also, aldimines of Formula (I), derived from hydroxy- and mercaptoamines—in which the primary amino groups are separated from the hydroxyl group or the mercapto group by a chain of at least 5 atoms or by a ring, can exhibit very little cyclization.

The aldimines of Formula (I) are new, not previously described compounds, which can have advantageous properties. They can contain tertiary aldimino groups, which do not have any hydrogen atoms on the C atom that stands for the carbonyl group in the α-position and therefore cannot tautomerize to form enamino groups. As a result, these aldimino groups can represent especially well protected ("blocked") primary amino groups, which show only extremely little or no reactivity with compounds that are reactive to amino groups with exclusion of moisture. In addition, the aldimines of Formula (I) can have an amide, thioamide, urethane, thiourethane, urea or thiourea group. The aldimines of Formula (I) together with isocyanate groups can have a surprisingly long shelf life, for example, also together with aromatic isocyanate groups. This long shelf life may be due to the fact that the nitrogen atoms of amide, thioamide, urethane, thiourethane, urea and thiourea groups are hardly basic. In addition, the aldimines of Formula (I) can also have only a slight amine-like odor or no odor at relatively low molecular weight of the basic aldehyde ALD. In addition, the fact that the aldimines of Formula (I) in most cases are liquid compounds can be advantageous.

The aldimines of Formula (I) can have a long shelf life under proper conditions. For example, if moisture gains access, their aldimino groups can hydrolyze formally to form amino groups via intermediate stages, whereby the corresponding aldehydes ALD of Formula (IV), used for the production of aldimines, can be released. Since this hydrolysis reaction is reversible, and the chemical equilibrium lies clearly on the aldimine side, it can be assumed from this that in the absence of compounds that are reactive to amines, only a portion of the aldimino groups partially or completely hydrolyzes.

The aldimines of Formula (I) can be used very extensively. For example, they can be used wherever they can serve as a source of aldehydes ALD of Formula (IV) or of amines B of Formula (III). For example, they can be used in the function of protected amines, or protected aldehydes, in aldehyde- and/or amine-reactive systems, and can be deprived of protection specifically there if necessary. For example, they are used in systems in which compounds that react with primary amines are present. The protection removal is carried out hydrolytically, for example, by contact with atmospheric humidity or water, and can be catalyzed by acids.

In addition, aldimines of Formula (I) with m>0 can be used in the creation of further functionalized reaction products of these aldimines. Thus, aldimines of Formula (I) with m>0 are reacted with compounds that can participate in addition reactions with the group HX to form addition products. Exemplary compounds that can participate in such addition reactions can carry reactive groups, such as, for example, isocyanate groups, epoxide groups, anhydride groups, or more or less strongly activated double or triple bonds such as (meth)acrylate groups, acrylamide groups, 1-ethylnylcarbonyl groups, 1-propinylcarbonyl groups, maleimide groups, citraconimide groups, vinyl groups, isopropenyl groups or allyl groups. Such aldimino groups that carry addition products can be hydrolyzed, if necessary, to form aldehydes ALD of Formula (IV) and compounds with primary amino groups and then used for additional reactions, for example for cross-linking reactions.

Exemplary among these addition products are addition products AV of Formula (XII), which can be available from the reaction of at least one polyisocyanate, for example, a polyisocyanate P, as it is described in more detail in this document, with at least one aldimine of Formula (I a).

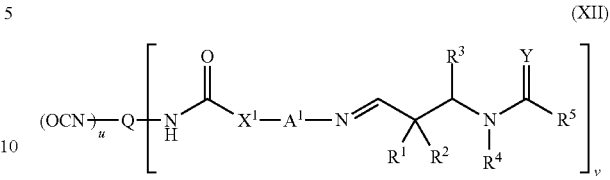

(XII)

wherein
u stands for 0 or 1 or 2 or 3,
v stands for 1 or 2 or 3 or 4,
provided that (u+v) stands for 2 or 3 or 4;
Q stands for the radical of a (u+v) polyisocyanate P that has isocyanate groups after removal of all isocyanate groups;
and $A^1$, $X^1$, Y, $R^1$, $R^2$, $R^3$, $R^4$ and $R^5$ have the already mentioned meanings.

Aldimines of Formula (I) and addition products AV of Formula (XII) can be used in compositions that are based on isocyanates. They can be used, for example, as latent curing agents or as co-monomers in one- or two-component compositions that have isocyanate groups, which are applied as adhesive, sealant, filling compound, coating, floor covering, paint, varnish, primer or foam.

As already mentioned, the aldimines of Formula (I) and their addition products can contain tertiary aldimino groups that do not tautomerize to form enamino groups and that represent especially well protected primary amino groups. Together with compounds that have isocyanate groups, the aldimines of Formula (I), with exclusion of moisture, can form long-shelf-life, i.e., largely viscosity-constant, mixtures, whereby it can be taken into consideration that the active hydrogen that is optionally contained in the aldimines (I) reacts with the isocyanate groups and in this case forms addition products, such as, for example, the addition products AV of Formula (XII). For example, mixtures that contain free aromatic isocyanate groups can also have a long shelf life.

A composition that includes a compound that has isocyanate groups and an aldimine of Formula (I) can react upon contact with moisture, for example, in the form of atmospheric humidity, under hydrolysis of aldimino groups; in this case, the isocyanate groups can react with the primary amino groups formally liberated by the hydrolysis of the aldimino groups to form urea groups, whereby an aldehyde ALD is released. Relative to the aldimino groups, excess isocyanate groups react directly with moisture and also form urea groups. With suitable stoichiometry between isocyanate groups and aldimino groups, the composition can cure as a result of these reactions; this process is also referred to as cross-linking. In this case, the reaction of the isocyanate groups with the hydrolyzing aldimino groups does not necessarily have to be carried out with free amino groups. Of course, reactions with intermediate stages of the hydrolysis reaction are also possible. For example, it is conceivable that a hydrolyzing aldimino group in the form of a semiaminal reacts directly with an isocyanate group.

After curing is completed, the released aldehyde ALD remains in the cured composition. It is extremely compatible with the latter, has little tendency to migrate or exude, and has only a slight softening effect, which can be advantageous.

Exemplary curing compositions, also called polyurethane compositions below, which contain at least one polyisocyanate and at least one aldimine of Formula (I), are disclosed. If the aldimine of Formula (I) has at least one HX group, it can also be present in the form of an addition product, for example, as addition product AV of Formula (XII).

In this document, substance names beginning with "poly," such as polyol, polyisocyanate or polyaldehyde, include substances that formally contain two or more of the functional groups per molecule that occur in their name.

In this document, the term "polyisocyanate" comprises compounds with two or more isocyanate groups, regardless of whether these are monomeric diisocyanates, oligomeric polyisocyanates or polymers that have isocyanate groups with a relatively high molecular weight.

In this document, the term "polymer" comprises, on the one hand, a collective of macromolecules that are chemically uniform but different relative to the degree of polymerization, molecular weight, and chain length, and said collective was produced by a polyreaction (polymerization, polyaddition, or polycondensation). The term also comprises derivatives of such a collective of macromolecules from polyreactions, i.e., compounds that were obtained by reactions, such as, for example, additions or substitutions, of functional groups on specified macromolecules, and that can be chemically uniform or chemically non-uniform. In addition, the term also comprises so-called prepolymers, i.e., reactive oligomeric prepolymers whose functional groups are involved in the creation of macromolecules.

The term "polyurethane polymer" comprises all polymers that are produced according to the so-called diisocyanate-polyaddition method. This also includes those polymers that are completely or almost free of urethane groups. Examples of polyurethane polymers are polyether polyurethanes, polyester polyurethanes, polyether polyureas, polyureas, polyester polyureas, polyisocyanurates and polycarbodiimides.

Exemplary aldimines that can be used as the aldimine of Formula (I) and their exemplary embodiments were previously described in detail. As an aldimine of Formula (I), the aldimines of Formula (I a) and the aldimines of Formula (I b) are exemplary.

Aldimines of Formula (I a), in which $HX^1$ stands for a hydroxyl or mercapto group, for example, for a hydroxyl group, as well as aldimines of Formula (I b), can be used. Aldimines of Formula (I b) can be used.

The polyurethane composition can be in single-component or two-component form. A two-component polyurethane composition has a component K1, which contains at least one polyisocyanate P, as it is described in detail herein, and a component K2, which contains at least one isocyanate-reactive substance. In the case of a two-component polyurethane composition, aldimines of Formula (I) can be present in the component K2. In the case of aldimines of Formula (I) with an index of m=0, for example, in aldimines of Formula (I b), this aldimine can be part of the component(s) K1 and/or K2, while aldimines of Formula (I), such as, for example, the aldimine of Formula (I a), with an index of m≠0, for example, cannot be present in the component K2 without a reaction being carried out with the polyisocyanate P.

As a polyurethane composition, a single-component, moisture-curing composition that contains
  a) at least one polyisocyanate P and
  b) at least one aldimine of Formula (I b), and/or at least one addition product AV of Formula (XII), can be used.

In this document, a curing composition—in which all integral parts of the composition are stored and/or mixed in the same barrels and which can have a shelf life over a longer period at room temperature, thus is not or is only insignificantly changed in its application or service properties by storage, and which can cure after application by the effect of moisture—is referred to as "single-component." A curing composition in which the two components, i.e., K1 or K2, in each case can be stored in separate barrels with a long shelf life, is referred to as "two-component."

In an exemplary embodiment, the polyisocyanate P is a polyurethane—polymer PUP that has isocyanate groups.

The term "polyurethane polymer" comprises all polymers that are produced according to the so-called diisocyanate-polyaddition method. This also includes those polymers that are completely or almost free of urethane groups. Examples of polyurethane polymers are polyether polyurethanes, polyester polyurethanes, polyether polyureas, polyureas, polyester polyureas, polyisocyanurates and polycarbodiimides.

A suitable polyurethane polymer PUP is available, for example, from the reaction of at least one polyol with at least one polyisocyanate. This reaction can be carried out in that the polyol and the polyisocyanate are brought to reaction with common methods, for example at temperatures of 50° C. to 100° C., optionally with the simultaneous use of suitable catalysts, whereby the polyisocyanate can be metered in such a way that its isocyanate groups are present in stoichiometric excess relative to the hydroxyl groups of the polyol. Advantageously, the polyisocyanate can be metered in such a way that an NCO/OH ratio of 1.3 to 5, for example, one of 1.5 to 3, is maintained. The "NCO/OH ratio" is defined as the ratio of the number of isocyanate groups used to the number of hydroxyl groups used. A content of free isocyanate groups of 0.5 to 15% by weight, for example, 0.5 to 5% by weight, for example, remains in the polyurethane polymer PUP after the reaction of all hydroxyl groups of the polyol.

The polyurethane polymer PUP optionally can be produced with simultaneous use of softeners, whereby the softeners that are used do not contain any groups that are reactive to isocyanate groups.

As polyols for the production of a polyurethane polymer PUP, for example, the following polyols or mixtures thereof can be used:

Polyoxyalkylene polyols, also called polyether polyols or oligoetherols, which are polymerization productions of ethylene oxide, 1,2-propylene oxide, 1,2- or 2,3-butylene oxide, oxetane, tetrahydrofuran or mixtures thereof, optionally polymerized using a starter molecule with two or more active hydrogen atoms, such as, for example, water, ammonia, or compounds with several OH or NH groups, such as, for example, 1,2-ethanediol, 1,2- and 1,3-propanediol, neopentyl glycol, diethylene glycol, triethylene glycol, the isomeric dipropylene glycols and tripropylene glycols, the isomeric butanediols, pentanediols, hexanediols, heptanediols, octanediols, nonanediols, decanediols, undecanediols, 1,3- and 1,4-cyclohexanedimethanol, bisphenol A, hydrogenated bisphenol A, 1,1,1-trimethylolethane, 1,1,1-trimethylolpropane, glycerol, aniline, as well as mixtures of the above-mentioned compounds. Both polyoxyalkylene polyols, which have a low degree of unsaturation (measured according to ASTM D-2849-69 and indicated in milliequivalents of unsaturation per gram of polyol (mEq/g)), produced, for example, using so-called double metal cyanide complex catalysts (DMC Catalysts), and polyoxyalkylene polyols with a higher degree of unsaturation, produced, for example, using anionic catalysts, such as NaOH, KOH, CsOH or alkali alcoholates, can be used.

Polyoxyalkylene diols or polyoxyalkylene triols, for example, polyoxyethylene and polyoxypropylene di- and -triols, can be used.

Polyoxyalkylene diols and -triols with a degree of unsaturation that is lower than 0.02 mEq/g and with a molecular weight in the range of 1,000-30,000 g/mol, as well as polyoxypropylene diols and -triols with a molecular weight of 400-8,000 g/mol, can be used.

So-called ethylene-oxide-terminated ("EO-endcapped," ethylene oxide-endcapped) polyoxypropylene polyols can be used. The latter are special polyoxypropylene polyoxyethylene polyols, which are obtained, for example, in that pure polyoxypropylene polyols, for example, polyoxypropylene diols and -triols, are further alkoxylated after polypropoxylation reaction with ethylene oxide is completed and as a result have primary hydroxyl groups.

Styrene-acrylonitrile- or acrylonitrile-methylmethacrylate-plugged poly ether polyols.

Polyester polyols, also called oligoesterols, for example, produced according to known methods, for example, the polycondensation of hydroxycarboxylic acids or the polycondensation of aliphatic and/or aromatic polycarboxylic acids with divalent or multivalent alcohols.

The polyester polyols can include, for example, those produced from divalent to trivalent, for example, divalent, alcohols, such as, for example, ethylene glycol, diethylene glycol, propylene glycol, dipropylene glycol, neopentyl glycol, 1,4-butanediol, 1,5-pentandiol, 3-methyl-1,5-hexanediol, 1,6-hexanediol, 1,8-octanediol, 1,10-decanediol, 1,12-dodecanediol, 1,12-hydroxystearyl alcohol, 1,4-cyclohexanedimethanol, dimer fatty acid diol (dimer diol), hydroxypivalic acid neopentyl glycol ester, glycerol, 1,1,1-trimethylolpropane or mixtures of the above-mentioned alcohols, with organic di- or tricarboxylic acids, for example, dicarboxylic acids, or their anhydrides or esters, such as, for example, succinic acid, glutaric acid, adipic acid, trimethyladipic acid, suberic acid, azelaic acid, sebacic acid, dodecanedicarboxylic acid, maleic acid, fumaric acid, dimer fatty acid, phthalic acid, phthalic acid anhydride, isophthalic acid, terephthalic acid, dimethyl-terephthalate, hexahydrophthalic acid, trimellitic acid and trimellitic acid anhydride, or mixtures of the above-mentioned acids, as well as polyester polyols that include lactones, such as, for example, ε-caprolactone and starters such as the above-mentioned divalent or trivalent alcohols.

Exemplary polyester polyols can include polyester diols.

Polycarbonate polyols, as they are available by reaction of, for example, the above-mentioned alcohols—used to create polyester polyols—with dialkylcarbonates, diarylcarbonates or phosgene.

Block copolymers that carry at least two hydroxyl groups, which have at least two different blocks with polyether, polyester and/or polycarbonate structures of the above-described type, for example, polyether polyester polyols.

Polyacrylate and polymethacrylate polyols.

Polyhydroxy-functional fats and oils, for example, natural fats and oils, for example, castor oil; or—so-called oleochemical—polyols obtained by chemical modification of natural fats and oils, for example the epoxy polyester or epoxy polyether obtained by epoxidation of unsaturated oils and subsequent ring opening with carboxylic acids or alcohols, or polyols obtained by hydroformylation and hydrogenation of unsaturated oils; or polyols obtained from natural fats and oils by degradation processes such as alcoholysis or ozonolysis and subsequent chemical cross-linking, for example by re-esterification or dimerization, of the thus obtained degradation products or derivatives thereof. Suitable degradation products of natural fats and oils can include, for example, fatty acids and fatty alcohols, as well as fatty acid esters, for example, the methyl esters (FAME), which can be derivatized, for example, by hydroformylation and hydrogenation to form hydroxy fatty acid esters.

Polyhydrocarbon polyols, also called oligohydrocarbonols, such as, for example, polyhydroxy-functional polyolefins, polyisobutylenes, polyisoprenes; polyhydroxy-functional ethylene-propylene, ethylene-butylene or ethylene-propylene-diene copolymers, as they are produced, for example, by the Kraton Polymers Company; polyhydroxy-functional polymers of dienes, for example, 1,3-butadiene, which can be produced, for example, also from anionic polymerization; polyhydroxy-functional copolymers that include dienes such as 1,3-butadiene or diene mixtures and vinyl monomers, such as styrene, acrylonitrile, vinyl chloride, vinyl-acetate, vinyl alcohol, isobutylene and isoprene, for example, polyhydroxy-functional acrylonitrile/butadiene copolymers, as they can be produced, for example, from epoxides or amino alcohols and carboxyl-terminated acrylonitrile/butadiene copolymers (for example, commercially available under the name Hypro® (earlier, Hycar®) CTBN and CTBNX and ETBN of Nanoresins AG, Germany, or Emerald Performance Materials LLC); as well as hydrogenated polyhydroxy-functional polymers or copolymers of dienes.

These above-mentioned polyols can have a mean molecular weight of 250-30,000 g/mol, for example, 400-20,000 g/mol, and can have a mean OH functionality in the range of 1.6 to 3.

As polyols, polyether-, polyester-, polycarbonate- and polyacrylate polyols, for example, diols and triols, can be used. Exemplary are polyether polyols, for example, polyoxypropylene- and polyoxypropylene polyoxyethylene polyols, as well as liquid polyester polyols and polyether polyester polyols.

In addition to these above-mentioned polyols, small amounts of low-molecular divalent or multivalent alcohols, such as, for example, 1,2-ethanediol, 1,2- and 1,3-propanediol, neopentyl glycol, diethylene glycol, triethylene glycol, the isomeric dipropylene glycols and tripropylene glycols, the isomeric butanediols, pentanediols, hexanediols, heptanediols, octanediols, nonanediols, decanediols, undecanediols, 1,3- and 1,4-cyclohexanedimethanol, hydrogenated bisphenol A, dimer fatty alcohols, 1,1,1-trimethylolethane, 1,1,1-trimethylolpropane, glycerol, pentaerythritol, sugar alcohols, such as xylitol, sorbitol or mannitol, sugars such as saccharose, other polyhydric alcohols, low-molecular alkoxylating products of the above-mentioned divalent and multivalent alcohols, as well as mixtures of the above-mentioned alcohols can be simultaneously used in the production of the polyurethane polymer PUP. Small amounts of polyols with a mean OH functionality of more than 3, for example, sugar polyols, can also be simultaneously used.

As polyisocyanates for the production of a polyurethane polymer PUP that has isocyanate groups, aromatic or aliphatic polyisocyanates, for example, diisocyanates, can be used.

As aromatic polyisocyanates, the following can be used: for example, monomeric di- or triisocyanates, such as 2,4- and 2,6-toluoylene diisocyanate and any mixtures of these isomers (TDI), 4,4'-, 2,4'- and 2,2'-diphenylmethane-diisocyanate and any mixtures of these isomers (MDI), mixtures that include MDI and MDI homologs (MDI or PMDI polymers), 1,3- and 1,4-phenylene diisocyanate, 2,3,5,6-tetramethyl-1, 4-diisocyanatobenzene, naphthalene-1,5-diisocyanate (NDI), 3,3'-dimethyl-4,4'-diisocyanatodiphenyl (TODD, dianisidine-diisocyanate (DADI), 1,3,5-tris-(isocyanatomethyl)-benzene, tris-(4-isocyanatophenyl)-methane and tris-(4-isocyanatophenyl)-thiophosphate, oligomers and polymers of the above-mentioned isocyanates, as well as any mixtures of the above-mentioned isocyanates. MDI and TDI can be used.

As aliphatic polyisocyanates, the following can be used: for example, monomeric di- or triisocyanates, such as 1,4-tetramethylene diisocyanate, 2-methylpentamethylene-1,5-diisocyanate, 1,6-hexamethylene diisocyanate (HDI), 2,2,4- and 2,4,4-trimethyl-1,6-hexamethylene diisocyanate (TMDI), 1,10-decamethylene diisocyanate, 1,12-dodecamethylene diisocyanate, lysine and lysine ester diisocyanate, cyclohexane-1,3- and -1,4-diisocyanate, 1-methyl-2,4- and -2,6-diisocyanatocyclohexane, and any mixtures of these isomers ($HTD_1$ or $H_6TDI$), 1-isocyanato-3,3,5-trimethyl-5-isocyanatomethyl-cyclohexane (=isophorone diisocyanate or IPDI), perhydro-2,4'- and -4,4'-diphenylmethane diisocyanate (HMDI or $H_{12}MDI$), 1,4-diisocyanato-2,2,6-trimethylcyclohexane (TMCDI), 1,3- and 1,4-bis-(isocyanatomethyl)-cyclohexane, m- and p-xylylene diisocyanate (m- and p-XDI), m- and p-tetramethyl-1,3- and -1,4-xylylenediisocyanate (m- and p-TMXDI), bis-(1-isocyanato-1-methylethyl)-naphthalene, dimer- and trimer fatty acid isocyanates such as 3,6-bis-(9-isocyanatononyl)-4,5-di-(1-heptenyl)-cyclohexene (dimeryl diisocyanate), α,α,α',α',α'',α''-hexamethyl-1,3,5-mesitylene triisocyanate, oligomers and polymers of the above-mentioned isocyanates, as well as any mixtures of the above-mentioned isocyanates. HDI and IPDI can be used.

Polyurethane polymers PUP with aromatic isocyanate groups can be used.

In an exemplary embodiment, the polyisocyanate P is a polyisocyanate PI in the form of a monomeric di- or triisocyanate or an oligomer of a monomeric diisocyanate or a derivative of a monomeric diisocyanate, wherein as a monomeric di- or triisocyanate, for example, the above-mentioned aromatic and aliphatic di- and triisocyanates can be used.

As polyisocyanate PI, the following can be used: oligomers or derivatives of monomeric diisocyanates, for example, of HDI, IPDI, TDI and MDI. Commercially available types are for example, HDI biurets, for example as Desmodur® N 100 and N 3200 (by Bayer), Tolonate® HDB and HDB-LV (by Rhodia) and Duranate® 24A-100 (by Asahi Kasei); HDI-isocyanurates, for example as Desmodur® N 3300, N 3600 and N 3790 BA (all by Bayer), Tolonate® HDT, HDT-LV and HDT-LV2 (by Rhodia), Duranate® TPA-100 and THA-100 (by Asahi Kasei) and Coronate® HX (by Nippon Polyurethane); HDI-uretdiones, for example as Desmodur® N 3400 (by Bayer); HDI-iminooxadiazinediones, for example as Desmodur® XP 2410 (by Bayer); HDI-allophanates, for example as Desmodur® VP LS 2102 (by Bayer); IPDI-isocyanurates, for example in solution as Desmodur® Z 4470 (by Bayer) or in solid form as Vestanat® T1890/100 (by Degussa); TDI oligomers, for example as Desmodur® IL (by Bayer); as well as mixed isocyanurates based on TDI/HDI, for example as Desmodur® HL (by Bayer). In addition, the following can be used: forms of MDI (so-called "modified MDI") that are liquid at room temperature and that represent mixtures of MDI with MDI derivatives, such as, for example, MDI carbodiimides or MDI uretonimines or MDI urethanes, known, for example, under trade names such as Desmodur® CD, Desmodur® PF, Desmodur® PC (all by Bayer), as well as mixtures that include MDI and MDI homologs (polymeric MDI or PMDI), available under trade names such as Desmodur® VL, Desmodur® VL50, Desmodur® VL R10, Desmodur® VL R20 and Desmodur® VKS 20F (all by Bayer), Isonate® M 309, Voranate® M 229 and Voranate® M 580 (all by Dow) or Lupranat® M 10 R (by BASF).

The above-mentioned oligomeric polyisocyanates PI can represent mixtures of substances with different degrees of oligomerization and/or chemical structures. They can have a mean NCO functionality of 2.1 to 4.0 and can contain, for example, isocyanurate, iminooxadiazinedione, uretdione, urethane, biuret, allophanate, carbodiimide, uretonimine or oxadiazinetrione groups. These oligomers can have a low content of monomeric diisocyanates.

As polyisocyanate PI, the following can be used: forms of MDI that are liquid at room temperature, as well as the oligomers of HDI, IPDI and TDI, for example, the isocyanurates and the biurets.

In an exemplary embodiment, the polyisocyanate P is a mixture that can contain at least one polyurethane polymer PUP and at least one polyisocyanate PI, as they were previously described.

The polyisocyanate P can be present in the form of an aromatic polyurethane polymer PUP that has isocyanate groups.

The polyisocyanate P can be present in an amount of 5 to 95% by weight, for example, in an amount of 10 to 90% by weight, relative to the entire composition. In filled compositions, i.e., compositions that contain a filler, the polyisocyanate P cam be present in an amount of 5 to 60% by weight, for example, 10 to 50% by weight, relative to the entire composition.

In addition, besides at least one polyisocyanate P, the single-component, moisture-curing composition can comprise at least one aldimine of Formula (I b) and/or one addition product AV of Formula (XII), whereby the latter optionally is formed in situ from at least one aldimine of Formula (I a) and the polyisocyanate P.

In the single-component, moisture-curing composition, the ratio between the sum of the number of aldimino groups and HX groups and the number of isocyanate groups can be 0.1 to 1.1, for example, 0.2 to 0.9, for example, 0.5 to 0.9.

The single-component, moisture-curing composition optionally contains additional integral parts, for example, the adjuvants and additives that are usually used in polyurethane compositions, for example the following:

Softeners, for example, carboxylic acid esters, such as phthalates, for example, dioctyl phthalate, diisononyl phthalate, or diisodecyl phthalate, adipates, for example, dioctyl adipate, azelates and sebacates, organic phosphoric and sulfonic acid esters or polybutenes;

Non-reactive thermoplastic polymers, such as, for example, homo- or copolymers of unsaturated monomers, for example, from the group that comprises ethylene, propylene, butylene, isobutylene, isoprene, vinyl acetate and alkyl(meth)acrylates, for example, polyethylenes (PE), polypropylenes (PP), polyisobutylenes, ethylene vinyl acetate copolymers (EVA) and atactic poly-α-olefins (APAO);

Solvents;

Inorganic and organic fillers, for example ground or precipitated calcium carbonates, which optionally are coated with fatty acids, for example, stearates, barite ($BaSO_4$, also called heavy spar), quartz flour, calcinated kaolins, aluminum oxides, aluminum hydroxides, silicic acids, for example, highly dispersed silicic acids from pyrolysis processes, carbon black, for example, industrially-produced carbon black (referred to as "carbon black," below), PVC powder or hollow spheres;

Fibers, for example made of polyethylene;

Pigments, for example titanium dioxide or iron oxides;

Catalysts, which accelerate the hydrolysis of aldimino groups, for example, acids, for example, organic carboxylic acids such as benzoic acid, salicylic acid, or 2-nitrobenzoic acid, organic carboxylic acid anhydrides such as, for example, phthalic acid anhydride, hexahydrophthalic acid anhydride, and hexahydromethylphthalic acid anhydride, silyl esters of organic carboxylic acids, organic sulfonic acids such as, for example, methanesulfonic acid, p-toluenesulfonic acid, or 4-dodecylbenzenesulfonic acid, sulfonic acid esters, other organic or inorganic acids, or mixtures of the above-mentioned acids and acid esters;

Catalysts that accelerate the reaction of isocyanate groups, for example, organotin compounds such as dibutyltin diacetate, dibutyltin dilaurate, dibutyltin dichloride, dibutyltin diacetylacetonate and dioctyltin dilaurate, bismuth compounds such as, for example, bismuth trioctoate and bismuth tris(neodecanoate), and compounds that contain tertiary amino groups, such as 2,2'-dimorpholinodiethylether and 1,4-diazabicyclo[2.2.2]octane;

Rheology modifiers such as, for example, thickeners or thixotropic agents, for example urea compounds, polyamide waxes, bentonites or pyrogenic silicic acids;

Blocked amines, for example, in the form of ketimines, oxazolidines, enamines or other aldimines;

Desiccants, such as, for example, molecular sieves, calcium oxide, highly reactive isocyanates such as p-tosylisocyanate, orthoformic acid esters, alkoxysilanes such as tetraethoxysilane; organoalkoxysilanes, such as, for example, vinyltrimethoxysilane, and organoalkoxysilanes, which have a functional group in α-position to the silane group;

Adhesion promoters, for example, organoalkoxysilanes ("silanes"), such as, for example, epoxysilanes, vinyl silanes, (meth)acrylsilanes, isocyanatosilanes, carbamatosilanes, alkylsilanes, S-(alkylcarbonyl)-mercaptosilanes and aldiminosilanes, as well as oligomeric forms of these silanes;

Stabilizers to protect against heat, light and UV radiation;

Flame-retardant substances;

Surfactants such as, for example, wetting agents, flow enhancers, ventilating agents, or foam inhibitors;

Biocides such as, for example, algicides, fungicides, or substances that inhibit fungal growth.

When using such additional integral parts, it can be advantageous, for example, to ensure that the latter do not greatly impair the shelf life of the composition. This means that in an exemplary embodiment, during storage, these integral parts should not trigger to a significant extent the reactions that lead to cross-linking, such as hydrolysis of the aldimino groups or cross-linking of the isocyanate groups. For example, this means that in an exemplary embodiment, all of these integral parts do not contain any water or at most only trace amounts of water. It may be useful to dry certain integral parts chemically or physically before mixing into the composition.

The single-component, moisture-curing composition can contain at least one catalyst. The catalyst can be, for example, one of the above-mentioned acids, such as benzoic acid or salicylic acid, or one of the above-mentioned metal compounds, or one of the above-mentioned tertiary amines. It may very well be advantageous to use different catalysts or different types of catalysts.

The described single-component, moisture-curing composition cam ne produced and stored with exclusion of moisture. It can have a long shelf life, i.e., it can be stored over a period of, for example, several months with exclusion of moisture in a suitable package or arrangement, such as, for example, a drum, a bucket, a bag, a cartridge, or a bottle, without changing in its application properties or in its properties after curing to an extent that is relevant for its use. The shelf life can be determined by measuring viscosity or extrusion force.

As already mentioned, the aldimino groups that are present in the composition can have the property, upon contact with moisture, of formally hydrolyzing to form an aldehyde ALD of Formula (IV) and an amine B of Formula (III), whereby the latter reacts with the isocyanate groups. Relative to the aldimino groups, excess isocyanate groups can react directly with moisture and also form urea groups. As a result of these reactions, the composition can cure to form a solid material; this process is also referred to as cross-linking.

The moisture that is required for curing can either originate from air (atmospheric humidity) or the composition can be brought into contact with a water-containing component, for example, by smearing, for example with a smoothing agent, or by spraying, or a water-containing component can be added to the composition during the application, for example in the form of a water-containing paste, which is mixed in, for example, via a static mixer.

The composition can be cured by means of atmospheric humidity.

The single-component moisture-curing composition can cure without the formation of bubbles. The curing speed can be influenced by the type and amount of one or more optionally present catalysts, by the temperature that prevails during curing, and by the atmospheric humidity or the amount of added water.

The described single-component, moisture-curing composition can have a series of advantages. On the one hand, it can have a long shelf life; in a suitable barrel with exclusion of moisture, it can be stored for several months up to one year and remains usable in the intended way during this time. On the other hand, upon contact with moisture, the composition can cure quickly and completely to form a highly elastic, largely non-adhesive material with high strength, expansion, and a high modulus of elasticity. The aldehyde ALD of Formula (IV) that is released during curing can be very highly compatible in the composition. In an exemplary embodiment, it has only a slight softening effect on the cured composition and tends neither to exude nor to migrate. In an exemplary embodiment, with a relatively low molecular weight of the aldehyde ALD that is released during curing, little or even no odor develops before, during or after the curing, which is desirable or required for many applications of such compositions, for example, in interior spaces.

The described compositions can be used as adhesive, sealant, coating, floor covering, filling compound, paint, varnish, primer, or foam, for example, as adhesive, sealant, coating or floor covering.

They can be used, for example, for applications in which little or even no odor is tolerated and in which elastic properties with relatively high moduli of elasticity are desired or required.

Another exemplary aspect relates to a method for adhesive bonding a substrate S1 to a substrate S2, which comprises the steps:

i) application of the single-component, moisture-curing composition on a substrate S1;

ii) ensuring contact of the applied composition with a substrate S2 within the open time of the composition;

or i') application of the single-component, moisture-curing composition on a substrate S1 and on a substrate S2;

ii') ensuring contact of the applied composition together within the open time of the composition;

whereby the substrate S2 includes the same material or a different material as the substrate S1.

The "open time," in this document, refers to the time during which the composition can be processed, after the isocyanate groups of the polyisocyanate have come into contact with moisture.

Another exemplary aspect relates to a method for sealing. This comprises the step:
i") application of the single-component, moisture-curing composition between a substrate S1 and a substrate S2, in such a way that the composition is in contact with the substrate S1 and the substrate S2;
whereby the substrate S2 includes the same material or a different material as the substrate S1.

The sealant can be pressed into a so-called joint.

Another exemplary aspect relates to a method for coating a substrate S1. The latter comprises the step:
i'") application of the single-component, moisture-curing composition on a substrate S1 within the open time of the composition.

In these methods, suitable substrates S1 and/or S2 can include, for example
Glass, glass ceramic, concrete, mortar, brick, adobe, gypsum, and natural stone such as granite or marble;
Metals or alloys such as aluminum, steel, iron, nonferrous metals, galvanized metals;
Leather, textiles, paper, wood, resin-bonded wood products, resin-textile composite materials, and other so-called polymer composites;
Plastics such as polyvinyl chloride (hard and soft PVC), acrylonitrile-butadiene-styrene copolymers (ABS), SMC (sheet molding compounds), polycarbonate (PC), polyamide (PA), polyester, poly(methylmethacrylate) (PMMA), polyester, epoxide resins, polyurethanes (PUR), polyoxymethylene (POM), polyolefins (PO), polyethylene (PE) or polypropylene (PP), ethylene/propylene copolymers (EPM) and ethylene/propylene/diene terpolymers (EPDM), whereby the plastics can be surface-treated by means of plasma, corona or flame;
Coated substrates such as powder-coated metals or alloys; as well as paints and varnishes.

The substrates can be pretreated, if necessary, before the application of the composition. Such pretreatments can comprise, for example, physical and/or chemical cleaning methods, for example, grinding, sandblasting, brushing, or the like, or treatment with cleaning agents or solvents, or the application of an adhesion promoter, an adhesion promoter solution or a primer.

The application of the composition can be carried out in a broad temperature spectrum. For example, the composition can be applied at room temperature. The composition can also, however, be applied at lower as well as at higher temperatures.

An article can be produced from these described methods for adhesive bonding, sealing or coating—or from the use of one of the described compositions as adhesive, sealant, filling compound, coating, floor covering, paint, varnish, primer or foam.

This article can be, for example, a structure, for example, a structure above or below ground level, or an industrial item or a consumer item, for example, a window, a household appliance, or a means of transport, for example, a vehicle for water or land, for example, an automobile, a bus, a truck, a train or a boat, or an accessory of a means of transport, or an article of the furniture, textile or packaging industry.

EXAMPLES

Description of the Measuring Methods

Infrared spectra were measured on an FT-IR device 1600 by Perkin-Elmer (horizontal ATR measuring unit with ZnSe crystals). Liquid samples were applied in undiluted form as films, and solid samples were dissolved in $CH_2Cl_2$. The absorption bands are indicated in wave numbers ($cm^{-1}$) (measuring window: 4000-650 $cm^{-1}$).

$^1$H-NMR spectra were measured on a spectrometer of the Bruker DPX-300 type at 300.13 MHz; the chemical shifts δ are indicated in ppm relative to tetramethylsilane (TMS); coupling constants J are indicated in Hz. No distinction was made among true and pseudo-coupling patterns.

The viscosity was measured on a thermostated cone-plate-viscosimeter Physica UM (cone diameter 20 mm, cone angle 1°, cone tip-plate-interval 0.05 mm, shear rate 10 to 1000 $s^{-1}$).

The amine content, i.e., the total content of aldimino groups and free amino groups in the produced compounds, was determined titrimetrically (with 0.1N of $HClO_4$ in glacial acetic acid, against crystal violet), and it is indicated in mmol of N/g.

Production of Aldehydes

N-(2,2-Dimethyl-3-oxopropyl)-N-methylacetamide

In a round-bottom flask with a mounted reflux condenser and under nitrogen atmosphere, 20.0 g (0.17 mol) of 2,2-dimethyl-3-methylamino-propanal was introduced while being stirred. 30.0 g (0.52 mol) of acetic acid anhydride was slowly added in drops to this, the mixture was mixed wtih 0.1 g of para-toluenesulfonic acid, and it was heated for 1 hour to 120° C. After cooling to room temperature, the reaction mixture was mixed with 100 ml of water, neutralized with $Na_2CO_3$, extracted several times with ethyl acetate, and the combined organic phase was dried on $MgSO_4$ and concentrated by evaporation. The thus obtained brown oil was fractionated in a vacuum. The product distilled at an overhead temperature of 93-95° C. and a pressure of 3 mbar. Yield: 8.2 g (30% of theory) of colorless and almost odorless liquid, which crystallized when left to stand.

IR: 3418br, 2971, 2939, 2875, 2815, 1786, 2726, 2711 (CHO), 1718 (C=O aldehyde), 1624 (C=O amide), 1487, 1464, 1405, 1364, 1320, 1263, 1202, 1125, 1108, 1086, 1040, 1007, 973, 951, 923, 904, 873, 772, 733.

N-(2,2-Dimethyl-3-oxopropyl)-pyrrolidin-2-one

In a round-bottom flask with a mounted reflux condenser and under nitrogen atmosphere, 40.0 g (0.48 mol) of 2-pyrrolidinone, 39.2 g (0.48 mol) of 36% aqueous formaldehyde, and 37.3 g (0.52 mol) of isobutyraldehyde were introduced while being stirred vigorously, mixed with 10.0 g of concentrated hydrochloric acid, whereby the mixture vigorously boiled up. After boiling had subsided, the mixture was heated to boiling in an oil bath (100° C.), and was kept boiling overnight. The clear, yellow reaction mixture was neutralized with 2N NaOH, extracted twice with ethyl acetate, the combined organic phases were washed with brine, dried on $MgSO_4$, and completely concentrated by evaporation in a rotary evaporator. The dark-yellow oil that was obtained was fractionated in a vacuum. The product distilled at an overhead temperature of 71° C. and a pressure of 2·$10^{-2}$ mbar. Yield: 14.8 g (19% of theory) of a colorless and almost odorless liquid.

IR: 3429br, 2969, 2961sh, 2930, 2897, 2872, 2837sh, 2786, 2758, 2711 (CHO), 1720 (C=O aldehyde), 1678 (C=O amide), 1494, 1462, 1438sh, 1421, 1400, 1380, 1365, 1333, 1314, 1286, 1259, 1225, 1152, 1103, 1062, 1024, 1002, 992, 975, 935, 908, 890sh, 867, 772, 672.

$^1$H-NMR (CDCl$_3$, 300 K): δ 9.58 (s, 1H, CHO), 3.41 (s, 2H, NCH$_2$C(CH$_3$)$_2$), 3.33 (t, J=7.0, 2H,

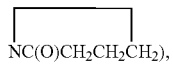

2.36 (t, J=8.1, 2 H,

1.99 (m, 2H,

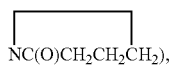

1.10 (s, 6H, NCH$_2$C(CH$_3$)$_2$).

N-(2,2-Dimethyl-3-oxopropyl)-azepan-2-one

In a round-bottom flask with a mounted reflux condenser and under nitrogen atmosphere, 80.5 g (0.71 mol) of ε-caprolactam, 59.3 g (0.71 mol) of 36% aqueous formaldehyde, and 56.4 g (0.78 mol) of isobutyraldehyde were introduced while being stirred vigorously, mixed with 13.4 g of concentrated hydrochloric acid (slight exothermicity). After that, the mixture was heated to boiling in an oil bath (100° C.) and was kept boiling overnight. The clear, yellowish reaction mixture was neutralized with 2N NaOH, extracted twice with ethyl acetate, the combined organic phases were washed with brine, dried on MgSO$_4$ and completely concentrated by evaporation in a rotary evaporator. The yellow oil that was obtained was fractionated in a vacuum. The product distilled at an overhead temperature of 98° C. and a pressure of 4·10$^{-2}$ mbar. Yield: 20.7 g (15% of theory) of colorless and odorless liquid, which crystallized when left to stand.

IR: 3415br, 2961, 2926, 2855, 2717 (CHO), 1720 (C=O aldehyde), 1635 (C=O amide), 1479, 1456, 1443, 1419, 1398, 1365, 1353, 1329, 1310, 1292sh, 1258, 1222, 1197, 1183, 1157, 1137, 1121, 1083, 1060, 1021, 998, 975, 969sh, 954, 944, 923, 909, 890, 872, 839, 815, 771, 735, 723, 703.

$^1$H-NMR (CDCl$_3$, 300 K): δ 9.55 (s, 1H, CHO), 3.47 (s, 2H, NCH$_2$C(CH$_3$)$_2$), 3.36 (m, 2H,

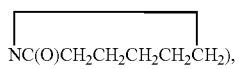

2.52 (m, 2H,

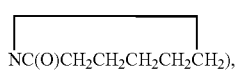

1.67 (m, 6H,

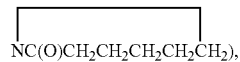

1.09 (s, 6H, NCH$_2$C(CH$_3$)$_2$).

N-(2,2-Dimethyl-3-oxopropyl)-N-methylformamide

In a round-bottom flask with a mounted reflux condenser and under nitrogen atmosphere, 59.7 g (1.00 mol) of N-methylformamide, 84.3 g (1.00 mol) of 36% aqueous formaldehyde, and 78.6 g (1.10 mol) of isobutyraldehyde were introduced while being stirred vigorously, mixed with 18.2 g of concentrated hydrochloric acid (slight exothermicity). After that, the mixture was heated to boiling in an oil bath (100° C.) and was kept boiling overnight. The clear, yellow reaction mixture was cooled to room temperature, neutralized with 2N NaOH, extracted twice with ethyl acetate; the combined organic phases were washed with brine, dried on MgSO$_4$, and completely concentrated by evaporation in a rotary evaporator. The dark-yellow oil that was obtained was fractionated in a vacuum. The product distilled at an overhead temperature of 63° C. and a pressure of 4·10$^{-2}$ mbar. Yield: 20.2 g (14% of theory) of colorless, slightly pungent-smelling liquid.

IR: 3412br, 2963, 2931, 2872, 2815sh, 2710 (CHO), 1724 (C=O aldehyde), 1667 (C=O amide), 1471, 1444, 1426sh, 1395, 1365, 1302, 1275, 1254, 1181, 1142, 1100, 1071sh, 1047, 990, 973, 953, 914, 883, 858, 772, 747, 710.

Production of Aldimines

Example 1

Aldimine A-1

In a round-bottom flask and under nitrogen atmosphere, 2.91 g (18.5 mmol) of N-(2,2-dimethyl-3-oxopropyl)-N-methylacetamide was introduced, and 1.28 g (15.4 mmol N) of 1,6-hexamethylenediamine solution (70% by weight in water; amine content 12.16 mmol of N/g) was stirred therein at room temperature. Then, the mixture was heated in an oil bath, and the volatile integral parts were removed in a vacuum (10 mbar, 80° C.). Yield: 3.45 g of pale yellow, almost odorless oil with an amine content of 4.74 mmol of N/g and a viscosity of 630 mPa·s at 20° C.

IR: 2959, 2930, 2854, 2827sh, 1644 (C=O, C=N), 1484, 1460, 1430, 1400, 1362, 1312, 1262, 1200, 1181sh, 1120, 1109, 1086, 1030, 1016, 978, 938, 904, 894, 860, 788, 764, 730.

Example 2

Aldimine A-2

Under the same conditions as described for aldimine A-1, 10.00 g (59 mmol) of N-(2,2-dimethyl-3-oxopropyl)-pyrrolidin-2-one was reacted with 4.00 g (49 mmol N) of 1,6-hexamethylenediamine (70% in water; amine content 12.16 mmol of N/g). Yield: 11.57 g of light yellow, almost odorless oil with an amine content of 4.13 mmol of N/g and a viscosity of 2.0 Pa·s at 20° C.

IR: 3410br, 2957, 2927, 2854, 2830sh, 1682 (C=O), 1666sh (C=N), 1493, 1461, 1434sh, 1418, 1392, 1363, 1331, 1313, 1284, 1261, 1222, 1150, 1108, 1057, 1023, 993, 944sh, 934, 911, 883, 854, 787, 758, 728, 675, 665.

$^1$H-NMR (CDCl$_3$, 300 K): δ 7.56 (t, J=1.3, 2 H, CH=N), 3.36 (t, J=7.0, 4H,

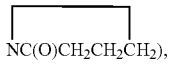

3.35 (t×d, J=7.0/1.3, 4 H, CH=N—CH$_2$), 3.32 (s, 4H, NCH$_2$C(CH$_3$)$_2$), 2.34 (t, J=8.1, 4H,

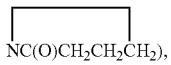

1.97 (m, 4H,

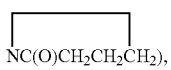

1.55 (m, 4H, CH=N—CH$_2$CH$_2$), 1.30 (m, 4H, CH=N—CH$_2$CH$_2$CH$_2$), 1.09 (s, 12H, NCH$_2$C(CH$_3$)$_2$).

Example 3

Aldimine A-3

Under the same conditions as were described for aldimine A-1, 12.67 g (64 mmol) of N-(2,2-dimethyl-3-oxopropyl)-azepan-2-one was reacted with 6.46 g (53 mmol N) of polyetherdiamine (Jeffamine® D-230, Huntsman; amine content 8.29 mmol of N/g) and concentrated by evaporation under high vacuum (4·10$^{-2}$ mbar) at 120° C. until a constant weight was reached. Yield: 16.50 g of yellow, odorless honey with an amine content of 3.18 mmol of N/g and a viscosity of 23.5 Pa·s at 20° C.

IR: 3420br, 2964, 2927, 2856, 1645 (C=O and C=N), 1480, 1465sh, 1455, 1444, 1417, 1392, 1367, 1328, 1310, 1291, 1260, 1228, 1196, 1133sh, 1104, 1096sh, 1084sh, 1015, 992, 975, 953, 939, 913, 879, 839, 817, 784, 735, 706.

$^1$H-NMR (CDCl$_3$, 300 K): δ 7.58 (m, 2H, CH=N), 3.6-2.8 (m, approximately 19.6; H, NCH$_2$C(CH$_3$)$_2$) and

and N/OCH$_2$CH(CH$_3$)), 2.50 (m, 4H,

1.75-1.55 (m, 12H,

1.15-1.05 (m, approximately 23.6H, NCH$_2$C(CH$_3$)$_2$ and N/OCH$_2$CH(CH$_3$)).

Example 4

Aldimine A-4

Under the same conditions as were described for aldimine A-1, 10.45 g (73 mmol) of N-(2,2-dimethyl-3-oxopropyl)-N-methylformamide was reacted with 5.05 g (61 mmol N) of 1,6-hexamethylenediamine solution (70% in water; amine content 12.16 mmol of N/g). Yield: 11.54 [g] of yellowish, slightly pungent-smelling oil with an amine content of 5.03 mmol of N/g and a viscosity of 1010 mPa·s at 20° C.

IR: 3430br, 2955, 2926, 2855, 2829, 1727, 1666 (C=O, C=N), 1465, 1443sh, 1424, 1390, 1362, 1339sh, 1303, 1273, 1254, 1221sh, 1182, 1162sh, 1143, 1093, 1067sh, 1046, 992, 975sh, 953, 932sh, 914, 865, 789, 744, 710, 658.

Example 5

Aldimine A-5

Under the same conditions as were described for aldimine A-1, 10.00 g (59 mmol) of N-(2,2-dimethyl-3-oxopropyl)-pyrrolidin-2-one was reacted with 5.07 g (48 mmol N) of 2-(2-aminoethoxy)-ethanol (DGA; Diglycolamine® agent, Huntsman; amine content 9.46 mmol of N/g). Yield: 14.11 g of light yellow, almost odorless oil with an amine content of 3.39 mmol of N/g and a viscosity of 630 mPa·s at 20° C.

IR: 3400br (OH), 2958, 2925, 2908, 2867, 1680sh (C=O), 1664 (C=N), 1493, 1463, 1438, 1421, 1393, 1363, 1332, 1314, 1287, 1262, 1226, 1123, 1060, 1024sh, 991, 946, 934, 899, 885, 858, 814, 788, 759, 674sh, 669.

$^1$H-NMR (CDCl$_3$, 300 K): δ 7.64 (t, J=1.3, 1H, CH=N), 3.71 and 3.57 (2×m, 2×4 H, HOCH$_2$CH$_2$OCH$_2$CH$_2$N), 3.40 (t, J=7.0, 2 H,

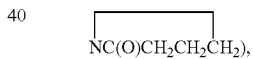

3.31 (s, 2H, NCH$_2$C(CH$_3$)$_2$), 2.35 (t, J=8.1, 2 H,

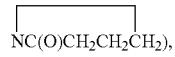

1.98 (m, 2H,

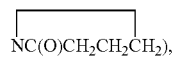

1.11 (s, 6H, NCH$_2$C(CH$_3$)$_2$).

Production of Curing Compositions

Examples 6 to 10 and Comparison Example 11

In a polypropylene beaker with a screw closure, either the polyurethane polymer P1 or the polyurethane polymer P2, whose production is described below, was mixed by means of a centrifugal mixer (SpeedMixer™ DAC 150, FlackTek Inc.; 1 minute at 2500 rpm) with an aldimine as well as with catalysts for forming a homogeneous mass; the thus obtained mass was immediately decanted in an aluminum tube that is varnished on the inside, and the latter was sealed in an airtight manner. The polyurethane polymers, aldimines and catalysts that are used for each of the examples are cited in parts by weight in Table 1.

The polyurethane polymer P1 was produced as follows:

4000 g of polyoxypropylene-diol (Acclaim® 4200 N, Bayer; OH number 28.5 mg of KOH/g) and 520 g of 4,4'-methylene diphenyl diisocyanate (4,4'-MDI; Desmodur® 44 MC L, Bayer) were reacted according to the known method at 80° C. to form an NCO-terminated polyurethane polymer with a content of free isocyanate groups of 1.9% by weight.

The polyurethane polymer P2 was produced as follows:

590 g of polyol Acclaim® 4200 N (polypropylene oxide diol, OH number 28.5 mg of KOH/g; Bayer), 1180 g of polyol Caradol® MD34-02 (polypropylene-oxide polyethylene oxide triol, OH number 35.0 mg of KOH/g; Shell) and 230 g of isophorone diisocyanate (IP DI; Vestanat® IPDI, Degussa) were reacted according to the known method at 80° C. to form an NCO-terminated polyurethane polymer with a content of free isocyanate groups of 2.1% by weight.

TABLE 1

Composition of Examples 6 to 11

| | Example | | | | | |
|---|---|---|---|---|---|---|
| | 6 | 7 | 8 | 9 | 10 | 11 (Cf.) |
| PUR-Polymer P1 | 50.0 | 50.0 | 50.0 | — | — | 50.0 |
| PUR-Polymer P2 | — | — | — | 50.0 | 50.0 | — |
| Aldimine | A-1, 3.34 | A-2, 3.84 | A-3, 4.97 | A-4, 3.47 | A-5, 2.58 | — |
| Salicylic Acid | 0.05 | 0.05 | 0.05 | 0.05 | 0.05 | — |
| Tin Catalyst$^a$ | 0.05 | 0.05 | 0.05 | 0.05 | 0.05 | — |
| [Aldimine/NCO]$^b$ | 0.70 | 0.70 | 0.70 | 0.70 | 0.35 | — |
| [(Aldimine + HX)/NCO]$^c$ | 0.70 | 0.70 | 0.70 | 0.70 | 0.70 | — |

$^a$5% by weight of dibutyltin dilaurate in diisodecyl phthalate.
$^b$Ratio between the number of aldimino groups and the number of isocyanate groups.
$^c$Ratio of the sum of the number of aldimino groups and HX groups to the number of isocyanate groups.

The thus obtained compositions were tested as follows:

As a measurement of the shelf life, the change in viscosity during storage in heat was determined. To this end, the composition was stored in the sealed tube in the furnace at 60° C., and the viscosity at 20° C. was measured a first time after 4 hours of storage time (="viscosity after 4 hours") and a second time after 7 days of storage time (="viscosity after 7 days"). The shelf life follows from the percentage increase of the second viscosity value relative to the first. To this end, the increase in viscosity is calculated in % according to the following formula:

[(Viscosity after 7 d/Viscosity after 4 h)−1]×100%.

To measure the skin formation time (time until freedom from adhesion, "tack-free time"), a small portion of the composition, stored for 4 hours at 60° C., was applied in a layer thickness of approximately 2 mm on cardboard, and in a normal climate (23±1° C., 50±5% relative atmospheric humidity), the time was determined that it took until no more residues were left on the pipette when the surface of the composition was tilted slightly by means of a pipette made of LDPE.

To determine the mechanical properties, a film with an approximately 3 mm thickness was produced with the main portion of the composition by the composition being poured into a flat PTFE mold and being cured for 7 days in a normal climate. Clear, tack-free and elastic polyurethane films were obtained, which were completely free of bubbles. Barbells with a length of 75 mm, a crosspiece length of 30 mm, and a crosspiece thickness of 4 mm were punched out from the film, and the latter were tested according to DIN EN 53504 for tensile strength, elongation at break, and E-modulus (at 0.5-5% expansion) (pulling speed: 200 mm/min).

In addition, the bubble formation (based on the amount of bubbles that occurred during the curing of the film) as well as the odor were evaluated qualitatively.

The results of these tests are cited in Table 2.

TABLE 2

Properties of Examples 6 to 11

| | Example | | | | | |
|---|---|---|---|---|---|---|
| | 6 | 7 | 8 | 9 | 10 | 11 (Cf.) |
| Viscosity after 4 h [Pa · s] | 33.1 | 32.0 | 29.5 | 23.1 | 38.7 | 35.3 |
| Viscosity after 7 d [Pa · s] | 38.0 | 34.2 | 33.3 | 30.0 | 58.0 | 38.1 |
| Increase in Viscosity [%] | 15 | 7 | 13 | 30 | 50 | 8 |
| Skin Formation Time [Min.] | 20 | 20 | 45 | 90 | 75 | >480 |
| Tensile Strength [MPa] | 3.5 | 2.1 | 1.4 | 1.4 | 1.2 | n.d. |
| Elongation at Break [%] | 590 | 550 | 720 | 330 | 450 | n.d. |
| E-Modulus [MPa] | 9.6 | 8.0 | 1.5 | 1.3 | 1.0 | n.d. |
| Bubble Formation | None | None | None | None | None | Many |
| Odor | Slight | Slight | None | Slight | Slight | None | n.d. stands for "not determined" (too many bubbles).

Thus, it will be appreciated by those skilled in the art that the present invention can be embodied in other specific forms without departing from the spirit or characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. An aldimine of Formula (I)

$$[HX]_m - A - \left[ N = \underset{R^1}{\underset{|}{\overset{R^3}{\overset{|}{C}}}} - \underset{R^2}{\underset{|}{C}} - \underset{R^4}{\underset{|}{N}} - \overset{Y}{\overset{\|}{C}} - R^5 \right]_n \quad (I)$$

wherein

Y represents O or S;

A either represents the (n+m)-value radical of an amine after removal of n primary amino groups and m HX groups, or together with $R^7$ represents an (n+2*m)-value hydrocarbon radical with 3 to 20 C atoms, which optionally contains at least one heteroatom;

$R^1$ and $R^2$ either independently of one another in each case represents a monovalent hydrocarbon radical with 1 to 12 C atoms, or together represent a divalent hydrocarbon radical with 4 to 12 C atoms, which is part of an optionally substituted, carbocyclic ring with 5 to 8 C atoms;

$R^3$ stands for a hydrogen atom or an alkyl, cycloalkyl, arylalkyl or alkoxycarbonyl radical with 1 to 12 C atoms;

R⁴ and R⁵ either
- together represent a divalent radical with 2 to 10 C atoms that optionally has oxygen or sulfur atoms and that is part of an optionally substituted, 5- or 6- or 7-membered ring, or
- R⁴ represents an alkyl, cycloalkyl, arylalkyl or acyl radical with 1 to 10 C atoms, and
- R⁵ represents a hydrogen atom or for a monovalent radical with 1 to 20 C atoms selected from the group consisting of an alkyl, cycloalkyl, arylalkyl, aryl radical, —OR⁵', —SR⁵' and —NR⁵'R⁵'',
  - wherein R⁵' and R⁵'' either in each case represents a hydrocarbon radical or together represent an alkylene radical, which is part of a 5-, 6- or 7-membered ring;

X represents O or S or N—R⁶ or N—R⁷,
- wherein R⁶
- either
  - represents a monovalent hydrocarbon radical with 1 to 20 C atoms, which has optionally at least one carboxylic acid ester, nitrile, nitro, phosphonic acid ester, sulfone or sulfonic acid ester group,
- or represents a substituent of Formula (II),

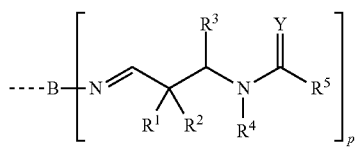

(II)

wherein
- p stands for 0 or for an integer from 1 to 10,000, and
- B stands for a (p+1)-value hydrocarbon radical, which optionally contains ether-oxygen, tertiary amine-nitrogen, hydroxyl groups, secondary amino groups or mercapto groups; and
- R⁷ together with A stands for an (n+2*m)-value hydrocarbon radical with 3 to 20 C atoms, which optionally contains at least one heteroatom;
- n stands for 1 or 2 or 3 or 4, and
- m stands for 0 or 1 or 2 or 3 or 4,
- provided that m+n stands for 2 or 3 or 4 or 5.

2. The aldimine according to claim 1, wherein R⁴ represents a methyl, ethyl, propyl, isopropyl, butyl, 2-ethylhexyl, cyclohexyl or benzyl radical, and
- wherein R⁵ represents hydrogen or a methyl, ethyl, propyl, isopropyl, butyl, 2-ethylhexyl, cyclohexyl, benzyl, methoxy, ethoxy, propoxy or isopropoxy radical.

3. The aldimine according to claim 1, wherein R⁴ and R⁵ together—with inclusion of the nitrogen atom and the carbonyl or thiocarbonyl group—form a 2-pyrrolidone ring, a pyrrolidine-2,5-dione ring, a piperidin-2-one ring, a piperidine-2,6-dione ring, an azepan-2-one ring, an oxazolidin-2-one ring or a thiazolidin-2-one ring, wherein such a ring is optionally substituted.

4. The aldimine according to claim 1, wherein the aldimine is represented by Formula (I a)

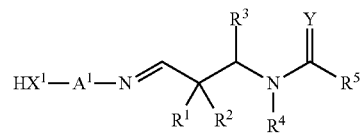

(I a)

wherein
A¹ either
- represents a divalent hydrocarbon radical with 2 to 20 C atoms, which optionally contains at least one heteroatom, or
- together with R⁹ represents a trivalent hydrocarbon radical with 3 to 20 C atoms, which optionally contains at least one heteroatom, X¹ represents O or S or N—R⁸ or N—R⁹,
- wherein R⁸
- either
  - represents a monovalent hydrocarbon radical with 1 to 20 C atoms, which optionally has at least one carboxylic acid ester, nitrile, nitro, phosphonic acid ester, sulfone or sulfonic acid ester group,
- or represents a substituent of Formula (II a),

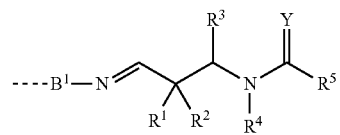

(II a)

wherein B¹ stands for a divalent hydrocarbon radical with 2 to 12 C atoms that optionally has ether-oxygen or tertiary amine-nitrogen; and
R⁹ together with A¹ represents a trivalent hydrocarbon radical with 3 to 20 C atoms, which optionally contains at least one heteroatom;
provided that A¹ does not have any active hydrogen.

5. The aldimine according to claim 4, wherein the aldimine is obtained from a reaction of at least one amine B1 that is selected from the group consisting of N-methyl-1,2-ethanediamine, N-ethyl-1,2-ethanediamine, N-cyclohexyl-1,2-ethanediamine, N-methyl-1,3-propanediamine, N-ethyl-1,3-propanediamine, N-butyl-1,3-propanediamine, N-cyclohexyl-1,3-propanediamine, 4-aminomethyl-piperidine, 3-(4-aminobutyl)-piperidine, diethylenetriamine (DETA), di-propylenetriamine (DPTA), bis-hexamethylenetriamine (BHMT), fatty diamines, 5-amino-1-pentanol, 6-amino-1-hexanol, 4-(2-aminoethyl)-2-hydroxyethylbenzene, 3-aminomethyl-3,5,5-trimethyl-cyclohexanol, 2-(2-aminoethoxy)-ethanol, triethylene glycol monoamine, 3-(2-hydroxyethoxy)-propylamine, 3-(2-(2-hydroxyethoxy)-ethoxy)-propylamine and 3-(6-hydroxyhexyloxy)-propylamine, with at least one aldehyde ALD of Formula (IV)

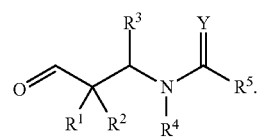

(IV)

6. The aldimine according to claim 1, wherein the aldimine is represented by Formula (I b),

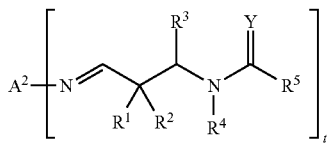

wherein
t represents 2 or 3;
A² represents a radical of an amine B2 after removal of t primary amino groups,
provided that the aldimine of Formula (I b) does not have any active hydrogen.

7. The aldimine according to claim 6, wherein the amine B2 is selected from the group consisting of 1,6-hexamethylenediamine, 1,5-diamino-2-methylpentane (MPMD), 1,3-pentanediamine (DAMP), 1-amino-3-aminomethyl-3,5,5-trimethylcyclohexane (=isophorone diamine or IPDA), 2,2,4- and 2,4,4-trimethylhexamethylenediamine (TMD), 1,3-xylylenediamine, 1,3-bis-(aminomethyl)cyclohexane, bis-(4-aminocyclohexyl)-methane, bis-(4-amino-3-methylcyclohexyl)-methane, 3(4),8(9)-bis-(aminomethyl)-tricyclo [5.2.1.0²,⁶]decane, 1,2-, 1,3- and 1,4-diaminocyclohexane, 1,4-diamino-2,2,6-trimethylcyclohexane, 3,6-dioxaoctane-1,8-diamine, 4,7-dioxadecane-1,10-diamine, 4-aminomethyl-1,8-octanediamine, polyoxyalkylene polyamines with two or three amino groups, 1,3- and 1,4-phenylenediamine, 2,4- and 2,6-toluoylenediamine, 4,4'-, 2,4'- and 2,2'-diaminodiphenylmethane, 3,3'-dichloro-4,4'-diaminodiphenylmethane and mixtures of the above-mentioned polyamines.

8. The aldimine according to claim 1, obtained from a reaction of at least one amine B1 or B2 with at least one aldehyde ALD of Formula (IV)

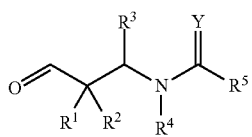

selected from the group consisting of N-(2,2-dimethyl-3-oxopropyl)-N-methylformamide, N-(2,2-dimethyl-3-oxopropyl)-N-methylacetamide, N-(2,2-dimethyl-3-oxopropyl)-N-butylacetamide, N-(2,2-dimethyl-3-oxopropyl)-N-(2-ethylhexyl)acetamide, N-(2,2-dimethyl-3-oxopropyl)-N-benzylacetamide, N-(2,2-dimethyl-3-oxopropyl)-N-methylbutyramide, N-(2,2-dimethyl-3-oxopropyl)-N-methyl-(2-ethylcapronamide), N-(2,2-dimethyl-3-oxopropyl)-N-methylbenzamide, O-ethyl-N-(2,2-dimethyl-3-oxopropyl)-N-methylcarbamate, N-(2,2-dimethyl-3-oxopropyl)-pyrrolidin-2-one, N-(2,2-dimethyl-3-oxopropyl)-piperidin-2-one, N-(2,2-dimethyl-3-oxopropyl)-azepan-2-one, N-(2,2-dimethyl-3-oxopropyl)-oxazolidin-2-one, N-(2,2-dimethyl-3-oxopropyl)-thiazolidin-2-one, N-(2,2-dimethyl-3-oxopropyl)-pyrrolidine-2,5-dione, and N-(2,2-dimethyl-3-oxopropyl)-phthalimide.

9. The aldimine according to claim 1, wherein the aldimine is obtained from an intermediate product ZW2 of Formula (X),

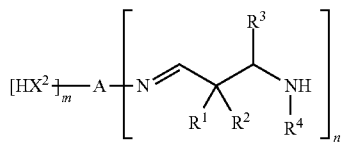

whereby X² represents O or S.

10. An addition product AV of Formula (XII), obtained from a reaction of at least one polyisocyanate P with at least one aldimine of Formula (I a) according to claim 4,

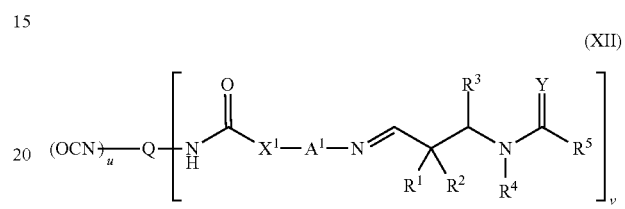

wherein Q represents a radical of a (u+v) polyisocyanate P that has isocyanate groups after removal of all isocyanate groups;
u represents 0 or 1 or 2 or 3,
v represents 1 or 2 or 3 or 4,
provided that (u+v) represents 2 or 3 or 4.

11. A single-component, moisture-curing composition, comprising
a) at least one polyisocyanate P, and
b) at least one aldimine of Formula (I b)

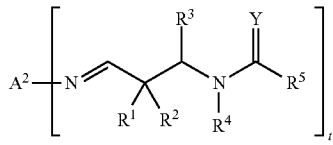

wherein
t represents 2 or 3;
A² represents a radical of an amine B2 after removal of t primary amino groups, provided that the aldimine of Formula (I b) does not have any active hydrogen,
Y represents O or S;
R¹ and R² either
  independently of one another in each case represents a monovalent hydrocarbon radical with 1 to 12 C atoms,
or together represent a divalent hydrocarbon radical with 4 to 12 C atoms, which is part of an optionally substituted, carbocyclic ring with 5 to 8 C atoms;
R³ stands for a hydrogen atom or an alkyl, cycloalkyl, arylalkyl or alkoxycarbonyl radical with 1 to 12 C atoms;
R⁴ and R⁵ either
  together represent a divalent radical with 2 to 10 C atoms that optionally has oxygen or sulfur atoms and that is part of an optionally substituted, 5- or 6- or 7-membered ring,
or
R⁴ represents an alkyl, cycloalkyl, arylalkyl or acyl radical with 1 to 10 C atoms, and R⁵ represents a hydrogen atom or for a monovalent radical with 1 to 20 C atoms selected from the group consisting of an alkyl, cycloalkyl, arylalkyl, aryl radical, —OR⁵', —SR⁵' and —NR⁵'R⁵",
  wherein R⁵' and R⁵" either in each case represents a hydrocarbon radical or together represent an alkylene radical, which is part of a 5-, 6- or 7-membered ring;
and/or at least one addition product AV of Formula (XII)

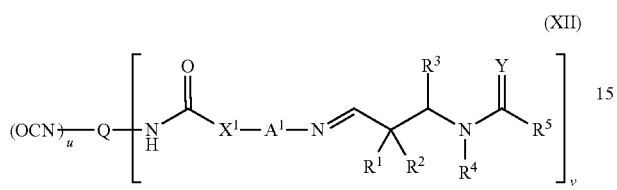

wherein Q represents a radical of a (u+v) polyisocyanate P that has isocyanate groups after removal of all isocyanate groups;
u represents 0 or 1 or 2 or 3,
v represents 1 or 2 or 3 or 4,
provided that (u+v) represents 2 or 3 or 4,
A¹ either
  represents a divalent hydrocarbon radical with 2 to 20 C atoms, which optionally contains at least one heteroatom,
  or
  together with R⁹ represents a trivalent hydrocarbon radical with 3 to 20 C atoms, which optionally contains at least one heteroatom,
X¹ represents O or S or N—R⁸ or N—R⁹,
  wherein R⁸
  either
    represents a monovalent hydrocarbon radical with 1 to 20 C atoms, which optionally has at least one carboxylic acid ester, nitrile, nitro, phosphonic acid ester, sulfone or sulfonic acid ester group,
  or represents a substituent of Formula (II a),

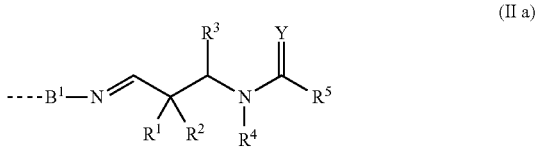

wherein B¹ stands for a divalent hydrocarbon radical with 2 to 12 C atoms that optionally has ether-oxygen or tertiary amine-nitrogen; and
R⁹ together with A¹ represents a trivalent hydrocarbon radical with 3 to 20 C atoms, which optionally contains at least one heteroatom;
provided that A¹ does not have any active hydrogen
Y represents O or S;
R¹ and R² either
  independently of one another in each case represents a monovalent hydrocarbon radical with 1 to 12 C atoms,
  or together represent a divalent hydrocarbon radical with 4 to 12 C atoms, which is part of an optionally substituted, carbocyclic ring with 5 to 8 C atoms;

R³ stands for a hydrogen atom or an alkyl, cycloalkyl, arylalkyl or alkoxycarbonyl radical with 1 to 12 C atoms;
R⁴ and R⁵ either
  together represent a divalent radical with 2 to 10 C atoms that optionally has oxygen or sulfur atoms and that is part of an optionally substituted, 5- or 6- or 7-membered ring,
  or
  R⁴ represents an alkyl, cycloalkyl, arylalkyl or acyl radical with 1 to 10 C atoms, and
  R⁵ represents a hydrogen atom or for a monovalent radical with 1 to 20 C atoms selected from the group consisting of an alkyl, cycloalkyl, arylalkyl, aryl radical, —OR⁵', —SR⁵' and —NR⁵'R⁵",
    wherein R⁵' and R⁵" either in each case represents a hydrocarbon radical or together represent an alkylene radical, which is part of a 5-, 6- or 7-membered ring.

12. The single-component, moisture-curing composition according to claim 11, wherein the polyisocyanate P represents a polyurethane polymer PUP that comprises aromatic isocyanate groups and that is obtainable from a reaction of at least one polyol with at least one aromatic monomeric diisocyanate.

13. A method for adhesive bonding a substrate S1 to a substrate S2, comprising:
  i) applying a single-component, moisture-curing composition on a substrate S1; and
  ii) ensuring contact of the applied composition with a substrate S2 within the open time of the composition;
  or
  i') applying a single-component, moisture-curing composition on a substrate S1 and on a substrate S2; and
  ii') ensuring contact of the applied composition on the substrate S1 with the applied composition on the substrate S2 within the open time of the composition;
  wherein the substrate S2 is of the same material as or a different material from a material of the substrate S1,
  wherein the single-component, moisture-curing composition is the single-component, moisture-curing composition of claim 11.

14. A cured composition obtained from a reaction of a single-component, moisture-curing composition according to claim 11 with moisture.

15. A method comprising forming an adhesive, sealant, coating or floor covering from at least the aldimine of Formula (I) according to claim 1.

16. The aldimine according to claim 1, wherein A together with R⁷ represents an (n+2*m)-value hydrocarbon radical with 3 to 20 C atoms, which contains at least one heteroatom in the form of ether-oxygen or tertiary amine-nitrogen.

17. The aldimine according to claim 1, wherein R¹ and R² together represent a divalent hydrocarbon radical with 4 to 12 C atoms, which is part of an optionally substituted, carbocyclic ring with 6 C atoms.

18. The aldimine according to claim 1, wherein R⁷ together with A stands for an (n+2*m)-value hydrocarbon radical with 3 to 20 C atoms, which contains at least one heteroatom in the form of ether-oxygen or tertiary amine-nitrogen.

19. The aldimine according to claim 4, wherein A¹ represents a divalent hydrocarbon radical with 2 to 20 C atoms, which contains at least one heteroatom in the form of ether-oxygen or tertiary amine-nitrogen.

20. The aldimine according to claim 4, wherein A¹ together with R⁹ represents a trivalent hydrocarbon radical with 3 to 20

C atoms, which contains at least one heteroatom in the form of ether-oxygen or tertiary amine-nitrogen.

21. The aldimine according to claim 4, wherein $R^9$ together with $A^1$ represents a trivalent hydrocarbon radical with 3 to 20 C atoms, which contains at least one heteroatom in the form of ether-oxygen or tertiary amine-nitrogen.

22. The aldimine according to claim 5, wherein the at least one amine B1 comprises a fatty diamine selected from the group consisting of N-cocoalkyl-1,3-propanediamine, N-oleyl-1,3-propanediamine, N-soya alkyl-1,3-propanediamine and N-tallowalkyl-1,3-propanediamine.

23. The cured composition according to claim 14, wherein the moisture is in the form of atmospheric humidity.

24. A method comprising forming an adhesive, sealant, coating or floor covering from at least the addition product AV of Formula (XII) according to claim 10.

* * * * *